(12) United States Patent
Matsuzaki et al.

(10) Patent No.: US 11,633,699 B2
(45) Date of Patent: Apr. 25, 2023

(54) DIALYZER, LIPOSOME PRODUCING APPARATUS, AND LIPOSOME PRODUCING METHOD

(71) Applicant: OSAKA UNIVERSITY, Osaka (JP)

(72) Inventors: Takashi Matsuzaki, Suita (JP); Tetsuo Minamino, Suita (JP); Ryo Araki, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 67 days.

(21) Appl. No.: 15/502,736

(22) PCT Filed: Aug. 5, 2015

(86) PCT No.: PCT/JP2015/072287
§ 371 (c)(1),
(2) Date: Feb. 8, 2017

(87) PCT Pub. No.: WO2016/024510
PCT Pub. Date: Feb. 18, 2016

(65) Prior Publication Data
US 2017/0232390 A1    Aug. 17, 2017

(30) Foreign Application Priority Data

Aug. 11, 2014 (JP) .............................. JP2014-163828

(51) Int. Cl.
*B01D 61/32* (2006.01)
*B01D 61/28* (2006.01)
(Continued)

(52) U.S. Cl.
CPC .............. *B01D 61/32* (2013.01); *A61K 9/127* (2013.01); *A61K 9/1278* (2013.01); *A61K 38/13* (2013.01);
(Continued)

(58) Field of Classification Search
CPC ...... B01D 61/32; B01D 61/243; B01D 61/28; B01D 63/02; B01D 2311/165;
(Continued)

(56) References Cited

U.S. PATENT DOCUMENTS 5,057,226 A * 10/1991 Antwiler ............ A61M 1/3486
210/641
5,094,854 A    3/1992 Ogawa et al.
(Continued)

FOREIGN PATENT DOCUMENTS

EP         0331505 A1 *  9/1989  ........... A61K 9/1272
JP      S54-088882 A     7/1979
(Continued)

OTHER PUBLICATIONS

International Search Report issued in PCT/JP2015/072287; dated Oct. 16, 2015.

*Primary Examiner* — Bobby Ramdhanie
*Assistant Examiner* — Donovan Bui-Huynh
(74) *Attorney, Agent, or Firm* — Studebaker & Brackett PC

(57) ABSTRACT

A dialyzer (15) includes a hollow fiber dialysis column (20), a liquid tubing section (12*a*), and a flow rate changing section (16*a*). The hollow fiber dialysis column (20) includes a hollow fiber membrane, a first flow channel that allows a dialysis target to flow internally of the hollow fiber membrane, and a second flow channel that allows an external liquid to flow externally of the hollow fiber membrane. The liquid tubing section (12*a*) tubes the dialysis target to an inlet (20*a*) of the first flow channel. The flow rate changing section (16*a*) is capable of changing a flow rate of the dialysis target at the dialysis target flowing out of an outlet (20*b*) of the first flow channel.

12 Claims, 13 Drawing Sheets

(51) Int. Cl.
- *A61K 9/127* (2006.01)
- *B01D 61/24* (2006.01)
- *B01D 63/02* (2006.01)
- *A61K 38/13* (2006.01)

(52) U.S. Cl.
CPC ............ *B01D 61/243* (2013.01); *B01D 61/28* (2013.01); *B01D 63/02* (2013.01); *B01D 2311/165* (2013.01); *B01D 2311/2649* (2013.01); *B01D 2313/243* (2013.01); *B01D 2313/50* (2013.01); *B01D 2315/10* (2013.01)

(58) Field of Classification Search
CPC ...... B01D 2311/2649; B01D 2313/243; B01D 2313/50; B01D 2315/10; B01D 63/021; B01D 63/022; B01D 2257/70; B01D 2313/08; B01D 2313/086; B01D 2321/22; B01D 2323/08; B01D 2325/028; B01D 61/145; B01D 61/18; B01D 61/20; B01D 61/22; B01D 63/06; B01D 63/061; B01D 67/0034; B01D 67/0062; B01D 67/0065; B01D 67/0088; B01D 69/02; B01D 69/141; B01D 71/024; A61K 38/13; A61K 9/127; A61K 9/1278; A61K 9/1277; A61K 31/573; A61K 9/1271; A61K 9/1272; A61M 1/14; A61M 1/16; A61M 1/3479; A61M 1/3482; A61M 1/361; A61M 1/3612; A61M 1/3621; A61M 1/3658; A61M 1/3693; A61M 1/3696; A61M 2206/11; A61M 1/1696; A61M 1/3472; A61M 1/3486; A61M 1/1623; A61M 1/1654; A61M 1/1656; A61M 1/1666; A61M 1/1668; A61M 1/1678; A61M 1/1698; A61M 1/267; A61M 1/287; A61M 1/30; A61M 1/302; A61M 1/303; A61M 1/309; A61M 1/3406; A61M 1/3427; A61M 1/3431; A61M 1/3458; A61M 1/3475; A61M 1/3489; A61M 1/36; A61M 1/3626; A61M 1/3639; A61M 1/3641; A61M 1/3643; A61M 1/3644; A61P 13/12; A61P 29/00; A61P 43/00; B01J 13/04; B01J 13/22; B01J 19/0046; B01J 2219/00515; B01J 2219/0052; B01J 2219/00524; B01J 2219/00547; B01J 2219/00585; B01J 2219/00596; B01J 2219/00605; B01J 2219/0061; B01J 2219/00612; B01J 2219/00617; B01J 2219/00619; B01J 2219/00621; B01J 2219/00626; B01J 2219/0063; B01J 2219/00637; B01J 2219/00641; B01J 2219/00644; B01J 2219/00659; B01J 2219/00664; B01J 2219/00673; B01J 2219/00707; B01J 2219/0072; B01J 2219/00722; B01J 2219/00731; B01J 3/50857; B01L 3/50857; C12Q 1/6837; C40B 40/06; C40B 40/12; C40B 70/00; G01N 2500/00; G01N 33/54313; G01N 33/5436; G01N 33/54366; G01N 1/4077; G01N 2001/4088; G01N 2333/4709; G01N 2800/2814; G01N 33/5304; G01N 33/6827; G01N 33/6893; Y10T 428/29; Y10T 436/143333; Y10T 436/25375; A61B 5/14532; C12N 2531/00; C12N 2533/54; C12N 2533/70; C12N 5/0686; Y10S 530/83

See application file for complete search history.

(56) References Cited

U.S. PATENT DOCUMENTS

| | | | |
|---|---|---|---|
| 2002/0039596 | A1 | 4/2002 | Hartounian et al. |
| 2006/0043007 | A1* | 3/2006 | Tarumi ................ A61M 1/3621 210/96.2 |
| 2007/0235889 | A1 | 10/2007 | Hartounian et al. |
| 2008/0035568 | A1* | 2/2008 | Huang ................ B01D 71/024 210/646 |
| 2009/0173682 | A1* | 7/2009 | Robinson ............ A61M 1/1621 210/240 |
| 2011/0139704 | A1* | 6/2011 | Choi .................... A61M 1/3639 210/416.1 |
| 2012/0267809 | A1* | 10/2012 | Shimizu ................ B01J 13/04 264/4.1 |
| 2014/0004173 | A1 | 1/2014 | Hartounian et al. |

FOREIGN PATENT DOCUMENTS

| | | |
|---|---|---|
| JP | H02-049718 A | 2/1990 |
| JP | H05-155758 A | 6/1993 |
| JP | H07-059849 A | 3/1995 |
| JP | H08-295697 A | 11/1996 |
| JP | 2001-522870 A | 11/2001 |
| JP | 2003-265597 A | 9/2003 |
| JP | 2005-225770 A | 8/2005 |
| JP | 2007-268257 A | 10/2007 |

* cited by examiner

|  | Conditions 1-1 | Conditions 1-2 | Conditions 1-3 |
|---|---|---|---|
| Flow rate at column inlet (mL/min.) | 2.00 | 2.00 | 2.00 |
| Flow rate at column outlet (mL/min.) | 2.00 | 1.33 | 3.00 |
| Flow rate of external liquid (mL/min.) | 60.0 | 60.0 | 60.0 |
| Position of waste liquid container | 110 cm below column | 110 cm below column | 110 cm below column |
| Waste liquid filter | Absent | Absent | Absent |
| Condensation ratio | 1.000 | 1.504 | 0.667 |
| Cyclosporine concentration (mg/mL) | 1.135 | 1.661 | 0.770 |

FIG. 9

|  | Conditions 2-1 | Conditions 2-1 |
|---|---|---|
| Flow rate at column inlet (mL/min.) | 2.00 | 2.00 |
| Flow rate at column outlet (mL/min.) | 2.00 | 2.00 |
| Flow rate of external liquid (mL/min.) | 40.0 | 60.0 |
| Position of waste liquid container | 110 cm below column | 110 cm below column |
| Waste liquid filter | Absent | Absent |
| Isopropanol concentration (% by mass) | 0.79 | 0.36 |

FIG. 11

|  | Conditions 3-1 | Conditions 3-2 |
|---|---|---|
| Flow rate at column inlet (mL/min.) | 2.00 | 2.00 |
| Flow rate at column outlet (mL/min.) | 2.00 | 2.00 |
| Flow rate of external liquid (mL/min.) | 60.0 | 60.0 |
| Position of waste liquid container | 110 cm below column | Same level as column |
| Waste liquid filter | Absent | Absent |
| Isopropanol concentration (% by mass) | 0.36 | 0.58 |

FIG. 12A

|  | Conditions 3-1 | Conditions 3-2 |
|---|---|---|
| Pressure at external flow channel inlet (mb) | 12 | 88 |
| Pressure at external flow channel outlet (mb) | -41 | 35 |
| Pressure at internal flow channel inlet (mb) | 15 | 97 |
| Pressure at internal flow channel outlet (mb) | -4 | 75 |

FIG. 12B

|  | Conditions 4-1 | Conditions 4-2 |
|---|---|---|
| Flow rate at column inlet (mL/min.) | 2.00 | 2.00 |
| Flow rate at column outlet (mL/min.) | 2.00 | 2.00 |
| Flow rate of external liquid (mL/min.) | 60.0 | 60.0 |
| Position of waste liquid container | 110 cm below column | 110 cm below column |
| Waste liquid filter | Absent | Present |
| Isopropanol concentration (% by mass) | 0.36 | 0.28 |

FIG. 13A

|  | Conditions 4-1 | Conditions 4-2 |
|---|---|---|
| Pressure at external flow channel inlet (mb) | 12 | 57 |
| Pressure at external flow channel outlet (mb) | −41 | 1 |
| Pressure at internal flow channel inlet (mb) | 15 | 59 |
| Pressure at internal flow channel outlet (mb) | −4 | 41 |

DIALYZER, LIPOSOME PRODUCING APPARATUS, AND LIPOSOME PRODUCING METHOD

TECHNICAL FIELD

The present invention relates to a dialyzer, a liposome producing apparatus, and apparatus and method for controlling a concentration of a dialysis target.

BACKGROUND ART

In order to remove for example an organic solvent and a non-encapsulated free drug in a liquid containing liposomes (referred to below as a liposome liquid), a method has been proposed for dialyzing the liposome liquid (dialysis target) using a hollow fiber dialysis column (see Patent Literatures 1 and 2, for example).

CITATION LIST

Patent Literature

[Patent Literature 1] Japanese Patent Application Laid-Open Publication No. 2-49718
[Patent Literature 2] Japanese Patent Application Laid-Open Publication No. 2005-225770

SUMMARY OF INVENTION

Technical Problem

The methods disclosed in Patent Literatures 1 and 2 can enable connection between the hollow fiber dialysis column and a liposome drug producing apparatus to achieve aseptic treatment on the liposome liquid in a short period of time through consistent operation. However, dilution or condensation of the liposome liquid in the course of dialysis may vary both concentrations of the drug and the liposomes (liposomes after dialysis) in the solution flowing out of the hollow fiber dialysis column. It is difficult to control a concentration of the liposome liquid after dialysis by the methods disclosed in Patent Literatures 1 and 2. For this reason, it is thought to be difficult to produce a liposome liquid having a desired concentration with high precision by the methods disclosed in Patent Literature 1 and 2. Furthermore, in a situation in which the liposome liquid after dialysis is condensed by a typical condensation method (for example, ultrafiltration or centrifugation) in order to adjust the concentration of the liposome liquid after dialysis, aggregation or fusion of the liposomes may tend to occur. Furthermore, it is necessary to take out of the liposome liquid from a sealed space. This makes it difficult to secure an aseptic state, takes long time for condensation, and complicates operation. For the reasons as above, such condensation methods are not suitable for liposome production on an industrial scale. In situation in which the concentration of the liposome liquid after dialysis is diluted, the liposome liquid may be diluted by adding for example water. However, it is difficult to uniformly stir a large amount of the solution in a secured aseptic state for yielding a liposome liquid having a desired concentration with high precision.

The present invention has been made in view of the foregoing problems and has its object of producing a dialysis target (for example, a liposome liquid) having a desired concentration by easily controlling a concentration of the dialysis target after dialysis (for example, a liposome liquid) in the course of dialysis using a hollow fiber dialysis column.

Solution to Problem

A dialyzer according to the present invention includes a hollow fiber dialysis column, a liquid tubing section, and a flow rate changing section. The hollow fiber dialysis column includes a hollow fiber membrane, a first flow channel that allows a dialysis target to flow internally of the hollow fiber membrane, and a second flow channel that allows an external liquid to flow externally of the hollow fiber membrane. The liquid tubing section tubes the dialysis target to an inlet of the first flow channel. The flow rate changing section is capable of changing a flow rate of the dialysis target at the dialysis target flowing out of an outlet of the first flow channel.

A liposome producing apparatus according to the present invention includes a production section configured to produce a liposome liquid containing liposomes, a purification section configured to purify the produced liposome liquid, and a collection section configured to collect the purified liposome liquid. The production section, the purification section, and the collection section are connected together in a sealable manner. The purification section includes a hollow fiber dialysis column and a flow rate changing section. The hollow fiber dialysis column includes a hollow fiber membrane, a first flow channel that allows a dialysis target to flow internally of the hollow fiber membrane, and a second flow channel that allows an external liquid to flow externally of the hollow fiber membrane. The flow rate changing section is capable of changing a flow rate of the dialysis target at the dialysis target flowing out of an outlet of the first flow channel.

A liposome producing apparatus according to the present invention incudes a production section configured to produce a liposome liquid containing liposomes, a purification section configured to purify the produced liposome liquid, and a collection section configured to collect the purified liposome liquid. The production section, the purification section, and the collection section are connected together in a sealable manner. The purification section includes a hollow fiber dialysis column. The hollow fiber dialysis column includes a hollow fiber membrane, a first flow channel that allows the liposome liquid to flow internally of the hollow fiber membrane, and a second flow channel that allows an external liquid to flow externally of the hollow fiber membrane. The external liquid in the second flow channel flows in a direction opposite to a direction in which the liposome liquid in the first flow channel flows. The liposome liquid passes through the first flow channel from an inlet to an outlet of the first flow channel only one time.

An apparatus for controlling a concentration of a dialysis target according to the present invention controls the concentration of the dialysis target using a hollow fiber dialysis column. The hollow fiber dialysis column includes a hollow fiber membrane, a first flow channel that allows the dialysis target to flow internally of the hollow fiber membrane, and a second flow channel that allows an external liquid to flow externally of the hollow fiber membrane. The apparatus for controlling a concentration of a dialysis target according to the present invention includes a control unit. The control unit causes the dialysis target to flow in the first flow channel and the external liquid to flow in the second flow channel and controls the concentration of the dialysis target flowing out of an outlet of the first flow channel based on a difference between a flow rate of the dialysis target at an inlet of the first flow channel and a flow rate of the dialysis target at the outlet of the first flow channel.

A method for controlling a concentration of a dialysis target according to the present invention is a method for controlling the concentration of the dialysis target using a hollow fiber dialysis column. The hollow fiber dialysis column includes a hollow fiber membrane, a first flow channel that allows the dialysis target to flow internally of the hollow fiber membrane, and a second flow channel that allows an external liquid to flow externally of the hollow fiber membrane. The method for controlling a concentration of a dialysis target according to the present invention controls the concentration of the dialysis target flowing out of an outlet of the first flow channel by causing the dialysis target to flow in the first flow channel and the external liquid to flow in the second flow channel for dialysis of the dialysis target and controlling at least one of an amount of liquid traveling from the first flow channel to the second flow channel and an amount of liquid traveling from the second flow channel to the first flow channel.

Advantageous Effects of Invention

According to the present invention, the dialysis target (for example, a liposome liquid) having a desired concentration can be produced by easily controlling the concentration of the dialysis target after dialysis (for example, a liposome liquid) in the course of dialysis using the hollow fiber dialysis column.

BRIEF DESCRIPTION OF DRAWINGS

FIG. 9 is a table listing experimental data in a first example of the present invention.

FIG. 11 is a table listing experimental data in a second example of the present invention.

FIGS. 12A and 12B each are a table indicating experimental data in a third example of the present invention.

FIGS. 13A and 13B each are a table indicating experimental data in a fourth example of the present invention.

DESCRIPTION OF EMBODIMENTS

The following describes an embodiment of the present invention with reference to the drawings.

Figure 1:
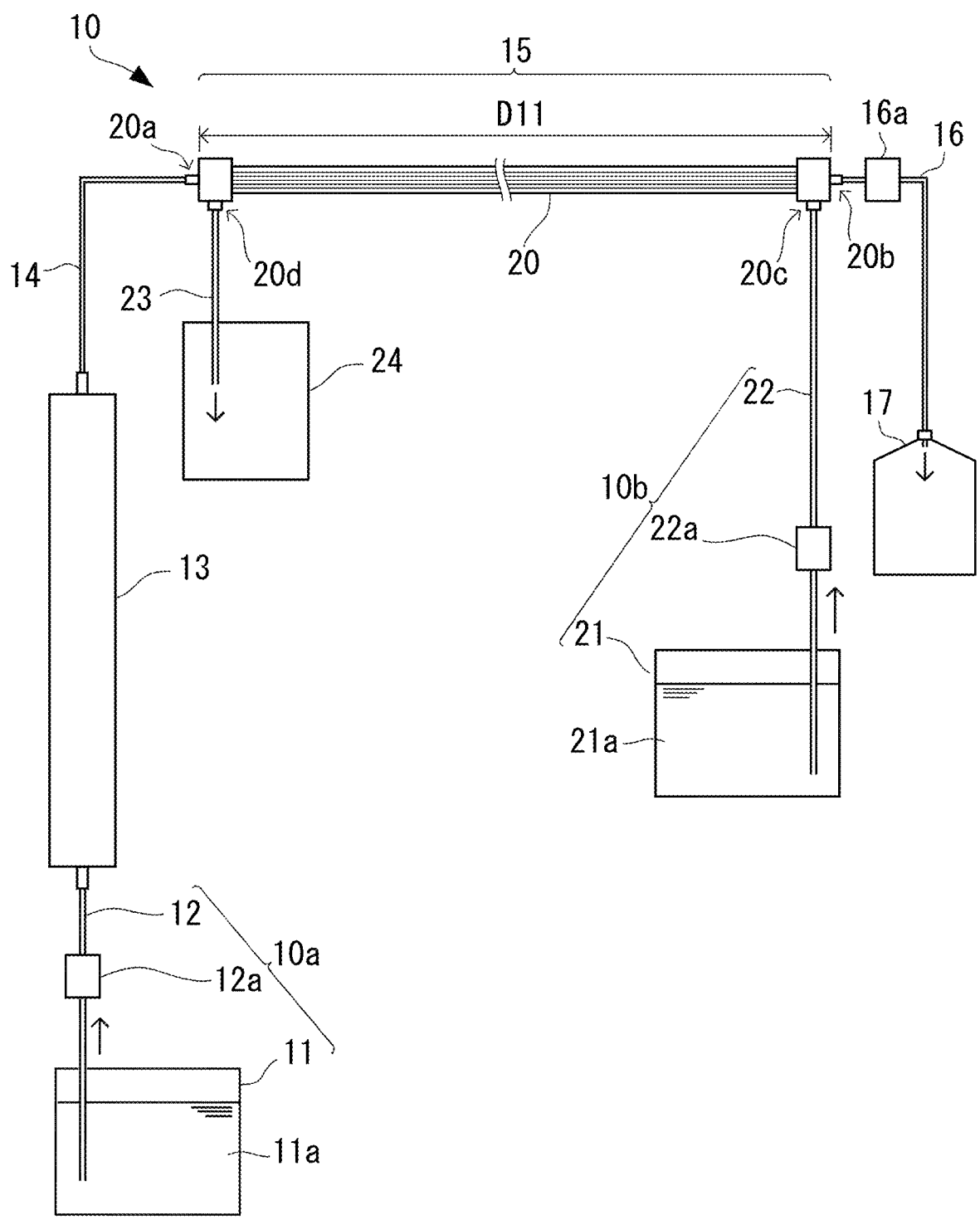
FIG. 1 is a diagram illustrating configuration of a liposome producing apparatus according to an embodiment of the present invention.

FIG. 1 illustrates a liposome producing apparatus 10 according to the present embodiment. The following describes configuration and operation of the liposome producing apparatus 10 with reference mainly to FIG. 1.

The liposome producing apparatus 10 according to the present embodiment includes a raw material supply section 10a, a production section 13, a purification section 15, and a collection section 17. The raw material supply section 10a includes a vessel 11, a tube 12, and a pump 12a (liquid tubing section).

The vessel 11 in the present invention is a sealable vessel. The vessel 11 has an injection port from which a raw material 11a (for example, a liquid raw material) is injected. An openable and closable lid is provided at the injection port of the vessel 11. The vessel 11 is sealed when the lid closes the injection port. The material of the vessel 11 is preferably selected in view of for example heat insulation (thermal conductivity), thermal resistance, chemical resistance, and airtightness.

The tube 12 is for example a liquid tubing pump tube (for example, "PharMed BPT" or "PharmaPure" manufactured by Saint-Gobain K.K.). The tube 12 has an inner diameter of for example about 0.8 mm. Note that the tube 12 can have an inner diameter of any value. The tube 12 may have an inner diameter larger than 0.8 mm. A material of the tube 12 is preferably selected in view of for example heat insulation (thermal conductivity), thermal resistance, chemical resistance, and airtightness.

The pump 12a is for example a syringe pump, a plunger pump, a piston pomp, or a roller pump. Note that any pump can be adopted as the pump 12a.

The vessel 11 is connected upstream of the pump 12a through the tube 12. The production section 13 is connected downstream of the pump 12a through the tube 12. The pump 12a pumps the raw material 11a (tubes liquid) in the vessel 11 toward the production section 13 at a predetermined flow rate. Operation of the pump 12a causes the raw material 11a to flow toward the production section 13 through the tube 12.

The production section 13 produces a liposome liquid (dialysis target) containing liposomes. The purification section 15 purifies (specifically, dialyzes) the liposome liquid produced by the production section 13 (liposome liquid before dialysis). The collection section 17 collects the liposome liquid purified by the purification section 15 (liposome liquid after dialysis). The production section 13 and purification section 15 (specifically, a hollow fiber dialysis column 20) are connected together through a tube 14. The liposome liquid produced by the production section 13 flows into the purification section 15 (specifically, the hollow fiber dialysis column 20) through the tube 14. The purification section 15 (specifically, the hollow fiber dialysis column 20) and the collection section 17 are connected together through a tube 16. The liposome liquid purified by the purification section 15 (liposome liquid after dialysis) flows into the collection section 17 through the tube 16. The tubes 14 and 16 each are for example a liquid tubing pump tube (examples include "PharMed BPT" and "PharmaPure" manufactured by Saint-Gobain K.K.). Materials of the respective tubes 14 and 16 are preferably selected in view of for example heat insulation (thermal conductivity), thermal resistance, chemical resistance, and airtightness.

Examples of materials of the respective tubes 12, 14, and 16 include thermoplastic polymer (for example, polyvinyl chloride containing a plasticizer), thermoplastic elastomer (for example, polyvinyl chloride containing no plasticizer, a copolymer of styrene-ethylene-butylene and silicone oil, and polypropylene-based plastic containing petroleum USP), thermosetting rubbers (for example, siloxane polymer containing non-crystalline silica), and thermocoagulable fluororubbers.

Figure 2:
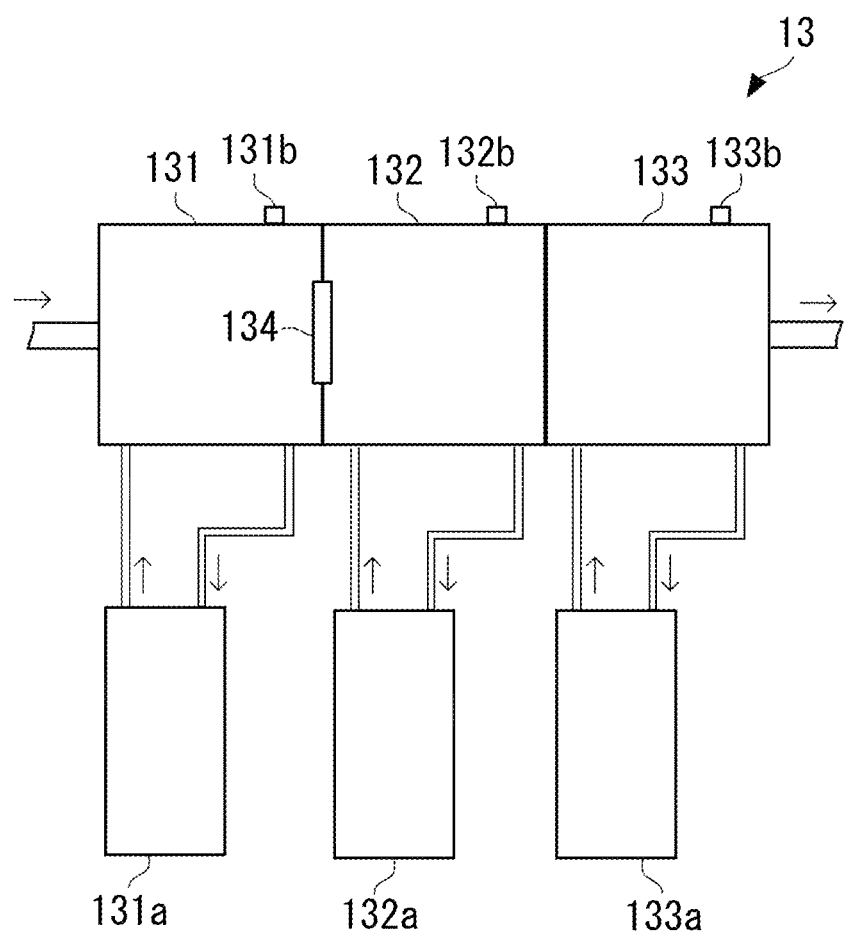
FIG. 2 is a diagram illustrating a production section of the liposome producing apparatus according to the embodiment of the present invention.

FIG. 2 illustrates an example of the production section 13. The example of the production section 13 will be described below with reference mainly to FIG. 2.

The production section 13 incudes for example a tanks 131, 132, and 133. The production section 13 further includes a sterilizing filter 134 at a boundary between the tanks 131 and 132. The tank 131 is a tank in which a row material is dissolved. The tank 132 is a tank in which liposomes are generated. The tank 133 is a cooling tank. The tanks 131, 132, and 133 are connected together for example through a pipe (examples include a helical stainless pipe), not illustrated. The raw material 11a (FIG. 1) flows through the pipe from the tank 131 (upstream) to the tank 133 (downstream). The tanks 131 to 133 each have heat insulation. The respective numbers of tanks in which the raw material is dissolved, tanks in which liposomes are generated, and cooling tanks are arbitrary and may be plural.

The tanks 131, 132, and 133 are connected to chillers 131a, 132a, and 133a, respectively. Furthermore, the tanks 131, 132, and 133 are provided with temperature sensors 131b, 132b, and 133b, respectively. The chillers 131a to 133a each adjust a heating medium (heat transfer medium or refrigerant) at a specific temperature and circulate the heating medium among the tanks 131, 132, and 133. Temperature control on the heating mediums in the respective chillers 131a, 132a, and 133a can result in temperature control on the respective tanks 131, 132, and 133.

The chiller 131a is capable of adjusting the temperature of the heating medium for example within a range of at least 30° C. and no greater than 95° C., preferably at least 50° C. and no greater than 95° C., and further preferably at least 70° C. and no greater than 85° C. The chiller 132a is capable of adjusting the temperature of the heating medium for example within a range of at least 0° C. and no greater than 50° C., preferably at least 5° C. and no greater than 30° C., and further preferably at least 15° C. and no greater than 25° C. The chiller 133a is capable of adjusting the temperature of the heating medium for example within a range of at least 0° C. and no greater than 50° C., preferably at least 5° C. and no greater than 30° C., and further preferably at least 15° C. and no greater than 25° C. Water can for example be used as the heating medium. However, the heating medium can be any medium and may be a liquid, a gas, or a solid (for example, an aluminum block).

The following describes an example of operation of the production section 13 with reference mainly to FIG. 2. In the example of the operation of the production section 13, a liposome liquid is produced using a solvent (water and water-miscible organic solvent) and a lipid as the raw material 11a.

The tank 131 is kept at a temperature (for example, at least 40° C. and no greater than 80° C.) at which a drug substance and the lipid (for example, phospholipid) of the raw material 11a are dissoluble in the solvent. The lipid of the raw material 11a is dissolved in the solvent in the tank 131. Through the above dissolution, a lipid solution is prepared. The prepared lipid solution is sent to the tank 132. Prior to generation of liposomes in the tank 132, the lipid solution passes through the sterilizing filter 134 to be sterilized.

The tank 132 is kept at a temperature (for example, at least 0° C. and lower than the temperature of the tank 131) at which liposomes are generated in the lipid solution. Liposomes are generated in the lipid solution in the tank 132. Through the above, a liposome suspension (liposome liquid) is prepared. The prepared liposome liquid is sent to the tank 133.

The tank 133 is kept at a temperature lower than the temperature of the tank 132 (for example, a temperature higher than 0° C. and lower than 40° C.) or equal to the temperature of the tank 132. The liposome liquid is cooled in the tank 133. Through the above cooling, the liposome liquid (at low temperature) containing the liposomes is yielded.

A liposome continuous production apparatus ("Lipo-TB" manufactured by Toray Engineering Co., Ltd.) can be adopted as a combination of the raw material supply section 10a and the production section 13.

Note that any method for producing a liposome liquid (liposomes) is adoptable. For example, the liposome liquid may be produced by a Bangham method (membrane method). An example of the Bangham method will be described below.

First, a lipid (for example, phospholipid) is dissolved in an organic solvent (for example, chloroform or dichloromethane). Subsequently, the lipid solution is charged into a flask. Next, the organic solvent in the flask is volatilized for example using a rotary evaporator. A lipid film is then formed at the bottom of the flask. Thereafter, a solution in which a drug is dissolved (for example, a buffer solution) is injected onto the lipid film. Through the above, the lipid is hydrated (or swelled). As a result, a suspension of liposomes (liposome liquid) is yielded.

The drug is encapsulated in lumens of the respective liposomes in the liposome liquid produced by the above method. However, the method is not limited to the above method. In an alternative method, it is possible to encapsulate the drug in the membranes of the liposomes in a manner that the drug is mixed with the lipid (for example, phospholipid) from the beginning and the mixture is dissolved in the organic solvent to form a film using the solution.

Figure 3A:
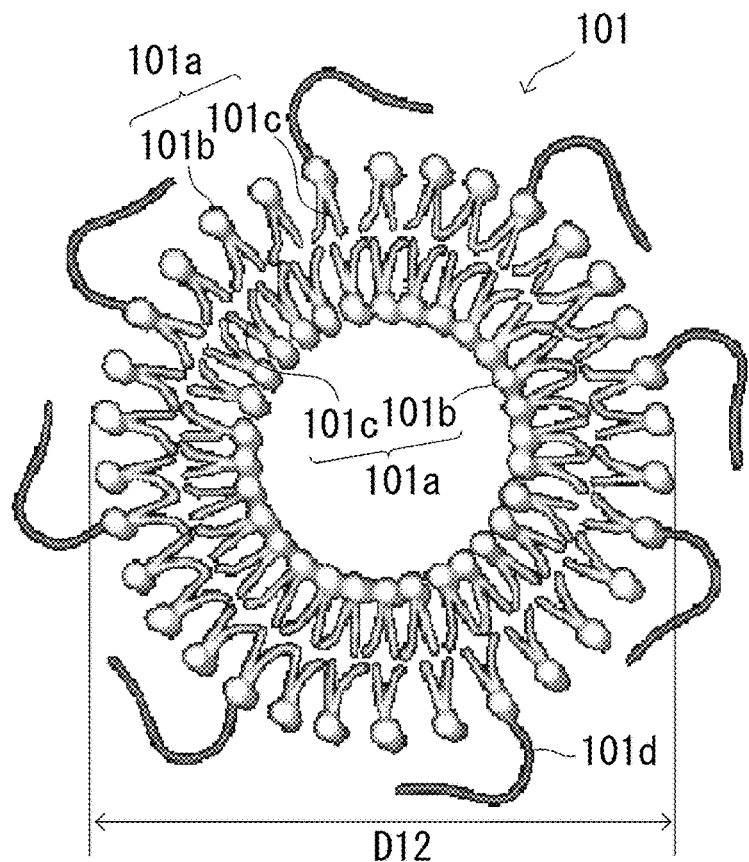
FIG. 3A is a diagram illustrating an example of a liposome.
Figure 3B:
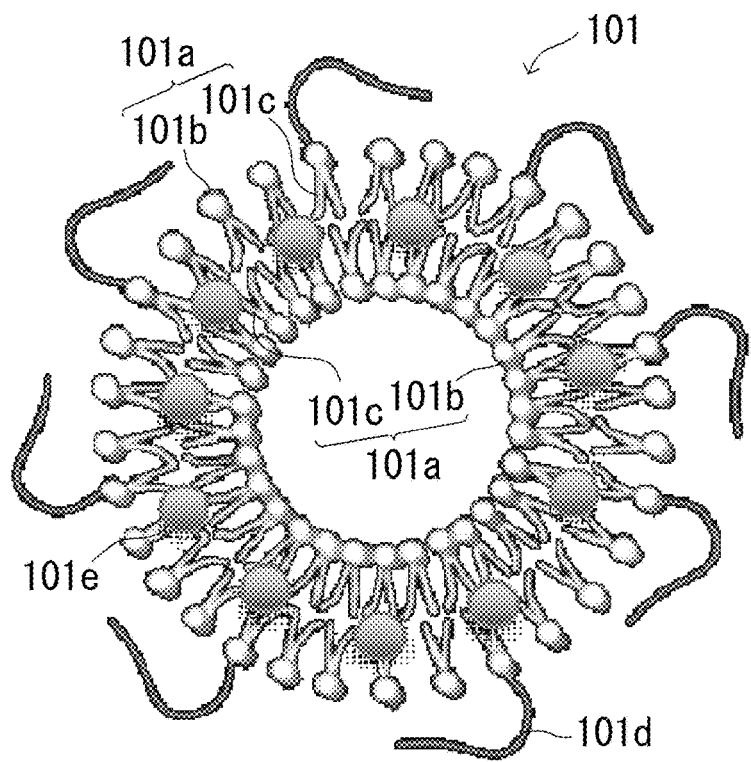
FIG. 3B is a diagram illustrating an example of a liposome in which a drug is encapsulated.

FIGS. 3A and 3B each illustrate an example of a liposome (liposome 101) contained in a liposome liquid. The liposome 101 will be described below with reference mainly to FIGS. 3A and 3B.

The liposome 101 includes a plurality of lipid molecules 101a. The lipid molecules 101a each have a hydrophilic portion 101b and a hydrophobic portion 101c. When the liposomes 101 are injected into a specific dispersion medium (for example, water), the lipid molecules 101a form a dual layer (referred to below as lipid dual layer) and the liposomes 101 each form into a spherical shape to have a minimum surface area. The hydrophilic portion 101b constitutes an outermost layer (referred to below as an outermost hydrophilic layer) and an innermost layer (referred to below as an innermost hydrophilic layer) in the lipid dual layer. By contrast, the hydrophobic portion 101c constitutes two layers (one of the layers located on the side of the innermost hydrophilic layer is referred to below as a first hydrophobic layer and the other layer located on the side of the outermost hydrophilic layer is referred to below as a second hydrophobic layer).

The liposome 101 is a substantially spherical hollow particle surrounded by the lipid dual layer. The liposomes 101 have for example an average particle diameter D12 of preferably at least 10 nm and no greater than 500 nm, more preferably at least 20 nm and no greater than 300 nm, and further preferably at least 30 nm and no greater than 200 nm. Note that the liposome 101 may be a liposome having a particle diameter of less than 100 nm (SUV: small unilameller vesicle), a liposome having a particle diameter of at least 100 nm (LUV: large unilamellar vesicle), or a multi-layered liposome (MLU: multilameller vesicle).

The liposome 101 may have a surface modified by a modifier 101*d*. The modifier 101*d* is constituted by for example polyethylene glycol (PEG) or a derivative thereof. The liposomes 101 modified by PEG or the derivative thereof tend to be retained in blood for a long period of time. Furthermore, when an antibody having high hydrophilicity to an affected tissue is connected to a PEG terminal, the liposomes 101 can be readily absorbed in an affected part. As a result, drug targeting property can be improved.

The lipid dual layer, which is analogous to a cell membrane forming a living body, can be readily accepted in an in vivo environment. For the reason as above, the liposomes 101 are used in a drug delivery system (DDS) in some cases. For example, when a drug 101*e* is encapsulated in the liposomes 101 as illustrated in FIG. 3B, the drug 101*e* can be transported to a specific in vivo part of a living body. The drug 101*e* is for example a composition of a therapeutic medicine for inflammatory disease. However, any type of drug can be used as the drug 101*e*. Examples of the drug 101*e* that can be used include an immunosuppressive agent, an antirheumatic drug, an anti-inflammatory enzyme preparation, a gout suppressant, an antihistamine drug, a chemical mediator release inhibitor, an anticancer agent, an anti-infective agent, and adenosine. Note that the liposomes 101 are used for any purpose. For example, a cosmetic may be manufactured using the liposomes 101.

The purification section 15 will be described below with reference mainly to FIGS. 1 and 4.

As illustrated in FIG. 1, the purification section 15 includes the hollow fiber dialysis column 20, a dialysate supply section 10*b*, and a waste liquid container 24.

Figure 4:
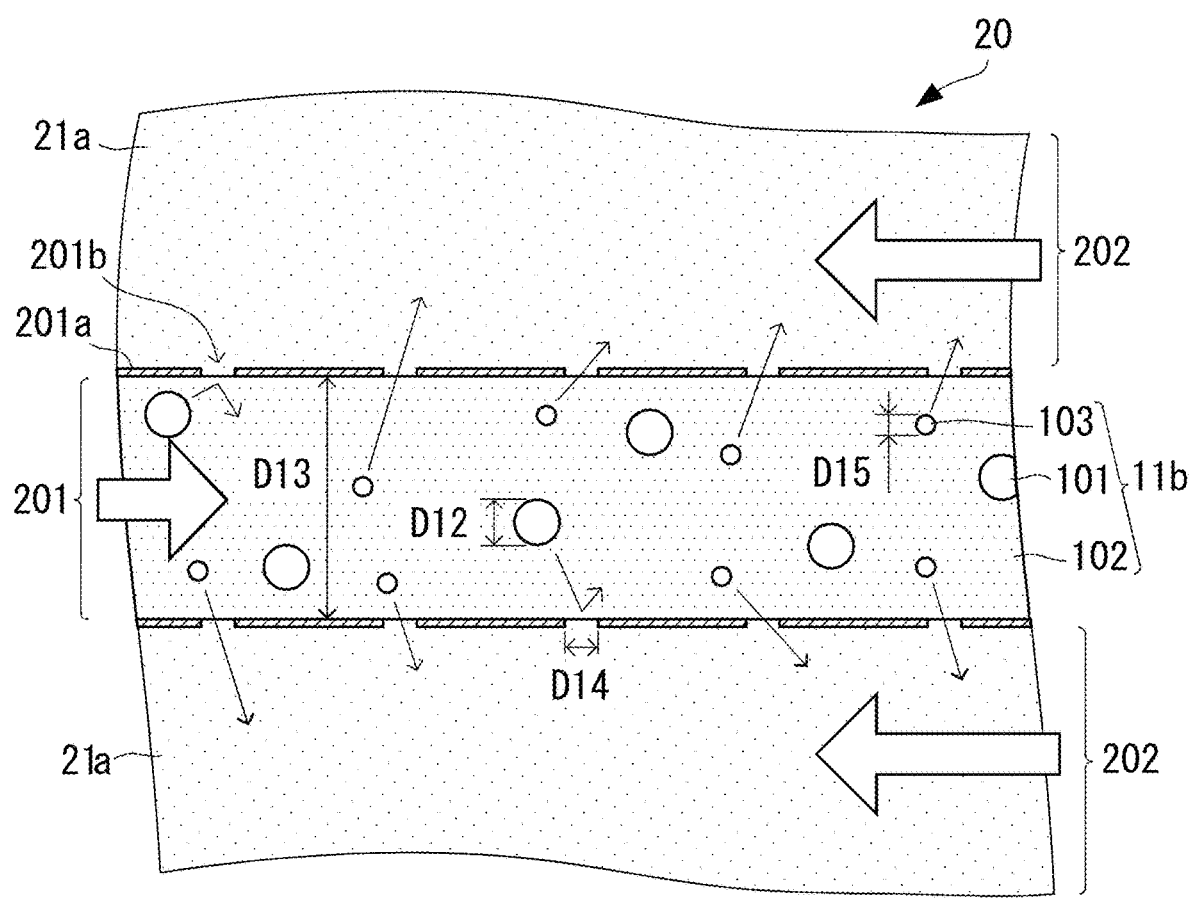
FIG. 4 is a diagram illustrating an example of a hollow fiber dialysis column of a dialyzer according to the embodiment of the present invention.

FIG. 4 illustrates an example (dialyzer) of the hollow fiber dialysis column 20. Configuration of the hollow fiber dialysis column 20 will be described below with reference mainly to FIGS. 1 and 4.

The hollow fiber dialysis column 20 includes in a housing thereof a mass of a plurality of hollow fiber membranes 201*a*. The hollow fiber membranes 201*a* (specifically, side surfaces of fibers) each have multiple pores 201*b*. The hollow fiber dialysis column 20 includes first flow channels 201 inside the respective hollow fiber membranes 201*a* and a second flow channel 202 outside the hollow fiber membranes 201*a*. The liposome liquid 11*b* (dialysis target) flows in the first flow channels 201. An external liquid 21*a* (dialysate) flows in the second flow channel 202. An inlet 20*a* is provided at upstream ends of the first flow channels 201, and an outlet 20*b* is provide at downstream ends thereof. An inlet 20*c* is provided at an upstream end of the second flow channel 202, and an outlet 20*d* is provided at a downstream end thereof. The inlet 20*c* of the second flow channel 202 is located in the vicinity of the outlet 20*b* of the first flow channels 201. The outlet 20*d* of the second flow channel 202 is located in the vicinity of the inlet 20*a* of the first flow channels 201.

The hollow fiber membranes 201*a* of the hollow fiber dialysis column 20 preferably have a MWCO (molecular weight cut off) of at least 3 kD and no greater than 750 kD, for example. The first flow channels 201 preferably each have a length from the inlet 20*a* to the outlet 20*b* of at least 10 cm and no greater than 300 cm, for example. A substantially long hollow fiber dialysis column 20 may be formed by connecting a plurality of hollow fiber dialysis columns in a longitudinal direction (in series). The hollow fiber membranes 201*a* each have an inner diameter (inner diameter of a fiber) D13 of at least 0.3 mm and no greater than 2.0 mm, for example. Furthermore, the pores 201*b* each have a diameter D14 smaller than an average particle diameter D12 of the liposomes 101, for example. For example, the pores 201*b* each preferably have a diameter D14 of at least 2 nm and no greater than 75 nm. Examples of a material of the hollow fiber membranes 201*a* include mPES (modified polyethersulfone), ME (mixed cellulose ester), PES (polyethersulfone), and PS (polysulfone). As the hollow fiber dialysis column 20, "MidiKros (registered Japanese trademark) module" manufactured by Spectrum Laboratories, Inc. can be adopted, for example.

Peripheral apparatuses of the hollow fiber dialysis column 20 will be described below with reference mainly to FIGS. 1 and 4.

The inlet 20*a* of the first flow channels 201 is connected downstream of the production section 13 through the tube 14. A pump 16*a* (flow rate changeable section) is provided downstream of the outlet 20*b* of the first flow channels 201. The outlet 20*b* of the first flow channels 201 is connected upstream of the pump 16*a* through the tube 16. The collection section 17 is connected downstream of the pump 16*a* through the tube 16.

The dialysate supply section 10*b* includes a vessel 21, a tube 22, and a pump 22*a*. The vessel 21 is a vessel for accommodating the external liquid 21*a* (dialysate). The vessel 21 in the present embodiment is a sealable vessel. The vessel 21 has an injection port from which the external liquid 21*a* is injected. An openable and closable lid is provided at the injection port of the vessel 21. When the lid closes the injection port, the vessel 21 is sealed. A material of the vessel 21 is preferably selected in view of for example heat insulation (thermal conductivity), thermal resistance, chemical resistance, and airtightness.

The pump 22*a* is for example a syringe pump, a plunger pump, a piston pump, or a roller pump. Any pump can be adopted as the pump 22*a*. The vessel 21 is connected upstream of the pump 22*a* through the tube 22. The hollow fiber dialysis column 20 (the inlet 20*c* of the second flow channel 202) is connected downstream of the pump 22*a* through the tube 22. The outlet 20*d* of the second flow channel 202 and the waste liquid container 24 are connected together through the tube 23.

Materials of the respective tubes 22 and 23 are preferably selected in view of for example heat insulation (thermal conductivity), thermal resistance, chemical resistance, and airtightness. Examples of the materials of the respective tubes 22 and 23 include thermoplastic polymer (for example, polyvinyl chloride containing a plasticizer), thermoplastic elastomer (for example, polyvinyl chloride containing no plasticizer, a copolymer of styrene-ethylene-butylene and silicone oil, and polypropylene-based plastic containing petroleum USP), thermosetting rubbers (for example, siloxane polymer containing amorphous silica), and thermocoagulable fluororubbers. The waste liquid container 24 (specifically, a location of the bottom of the container) is preferably located at a lower level (in a gravity direction) than the hollow fiber dialysis column 20 (specifically, a center of the column placed horizontally), and more preferably at a level at least 70 cm lower than the hollow fiber dialysis column (specifically, the center of the column placed horizontally). When the waste liquid container 24 is located at a lower level than the hollow fiber dialysis column 20 (preferably, at a level at least 70 cm lower than the hollow fiber dialysis column), dialysis efficiency tends to increase. The reason therefor is inferred to be that the external liquid 21*a* can readily flow out of the hollow fiber dialysis column 20.

It is preferable to provide a filter (waste liquid treating filter) at the outlet 20*d* of the second flow channel 202. When the filter is provided at the outlet 20*d* of the second flow channel 202, an internal pressure of the hollow fiber dialysis column 20 increases, so that dialysis efficiency tends to increase. An exemplary waste liquid treating filter (air passage filter) 25 is shown in, for example, FIGS. 6 and 7.

Operation of the purification section 15 will be described below with reference mainly to FIGS. 1 and 4. In the liposome producing apparatus 10 in the present embodiment, the purification section 15 filtrates (specifically, dialyzes) the liposome liquid by countercurrent dialysis using the hollow fiber membranes 201*a*.

As illustrated in FIG. 4, the liposome liquid 11*b* before dialysis produced by the production section 13 contains for example the liposomes 101, a dispersion medium 102 (for example, an aqueous medium), and organic particulates 103. The organic particulates 103 include for example a residual organic solvent (for example, isopropanol), a free drug (specific examples include cyclosporine, an antirheumatic drug, an anti-inflammatory enzyme preparation, a gout suppressant, an antihistamine drug, a chemical mediator release inhibitor, an anticancer agent, an anti-infective agent, and adenosine) not having been encapsulated in the liposomes, and a phospholipid. The organic particulates 103 each have a particle diameter D15 smaller than the diameter D14 of the pores 201*b*. The organic particulates 103 each have a particle diameter D15 of at least 1 nm and no greater than 8 nm, for example.

In a situation in which the liposome liquid 11*b* is dialyzed, the external liquid 21*a* is caused to flow externally of the hollow fiber membranes 201*a* along the hollow fiber membranes 201*a* (specifically, the side surfaces of fibers) by operating the pump 22*a*. The external liquid 21*a* is for example the same liquid (for example, an aqueous medium) as a medium (the dispersion medium 102) for dispersing the liposomes 101 in the liposome liquid 11*b* (dialysis target).

The pump 22*a* pumps the external liquid 21*a* (tubes liquid) in the vessel 21 toward the hollow fiber dialysis column 20. Operation of the pump 22*a* causes the external liquid 21*a* to flow toward the hollow fiber dialysis column 20 (the inlet 20*c* of the second flow channel 202) through the tube 22 and flow along the hollow fiber membranes 201*a* externally of the hollow fiber membranes 201*a* in the second flow channel 202. The external liquid 21*a* flows from the inlet 20*c* to the outlet 20*d* of the second flow channel 202, passes through the tube 23, and then is collected in the waste liquid container 24. Thereafter, the collected waste liquid is discarded. However, the collected waste liquid may be appropriately treated and the treated waste liquid may be reuse as the external liquid 21*a* (dialysate).

In a situation in which the liposome liquid 11*b* is dialyzed, the liposome liquid 11*b* is caused to flow internally of the hollow fiber membranes 201*a* (the first flow channels 201) along the hollow fiber membranes 201*a* (specifically, the side surfaces of fibers) while the external liquid 21*a* is caused to flow as described above. A direction in which the liposome liquid 11*b* flows is preferably opposite (reverse) to a direction in which the external liquid 21*a* flows. Causing the liposome liquid 11*b* and the external liquid 21*a* to flow in the opposite directions can increase dialysis efficiency.

The liposome liquid 11*b* flowing internally of the hollow fiber membranes 201*a* (the first flow channels 201) travels outward of the hollow fiber membranes 201*a* (toward the second flow channel 202) by diffusion. However, as illustrated in FIG. 4, the liposomes 101 in the liposome liquid 11*b* that are larger than the pores 201*b* cannot pass through the pores 201*b*. By contrast, the organic particulates 103 that are smaller than the pores 201*b* can pass through the pores 201*b*. As such, the organic particulates 103 contained in the liposome liquid 11*b* are removed out of the hollow fiber membranes 201*a*.

Further, the dispersion medium 102 in the liposome liquid 11*b* also travels from the inside (the first flow channels 201) to the outside (the second flow channel 202) of the hollow fiber membranes 201*a*. By contrast, the external liquid 21*a* travels from the outside (the second flow channel 202) to the inside (the first flow channels 201) of the hollow fiber membranes 201*a*. In the method for controlling a concentration of a dialysis target according to the present embodiment, the dialysis target is caused to flow in the first flow channels 201 and the external liquid 21*a* is caused to flow in the second flow channel 202 in the hollow fiber dialysis column 20 for dialysis of the dialysis target while the respective amounts of the liposome liquid 11*b* (dialysis target) flowing into the first flow channels 201 and the liposome liquid 11*b* (dialysis target) flowing out of the first flow channels 201 are controlled. This controls a difference between a travel amount of the dispersion medium 102 in the hollow fiber dialysis column 20 (amount of liquid moving from the first flow channels 201 to the second flow channel 202) and a travel amount of the external liquid 21*a* (amount of liquid moving from the second flow channel 202 to the first channels 201) and eventually controls the concentration of the dialysis target (specific operation will be described later).

The dialyzed liposome liquid 11*b* having flown from the inlet 20*a* to the outlet 20*b* of the first flow channels 201 (liposome liquid 11*b* after dialysis) flows into the collection section 17 through the tube 16.

The liposome producing apparatus 10 in the present embodiment does not circulate the liposome liquid 11*b* that has been once dialyzed. Specifically, the liposome liquid 11*b* after dialysis flowing out of the outlet 20*b* of the first flow channels 201 is not returned to the inlet 20*a* of the first flow channels 201. In the above configuration, the liposome liquid 11*b* passes through the first flow channels 201 from the inlet 20*a* to the outlet 20*b* thereof only one time. The above configuration can reduce time taken for purification.

Figure 5:
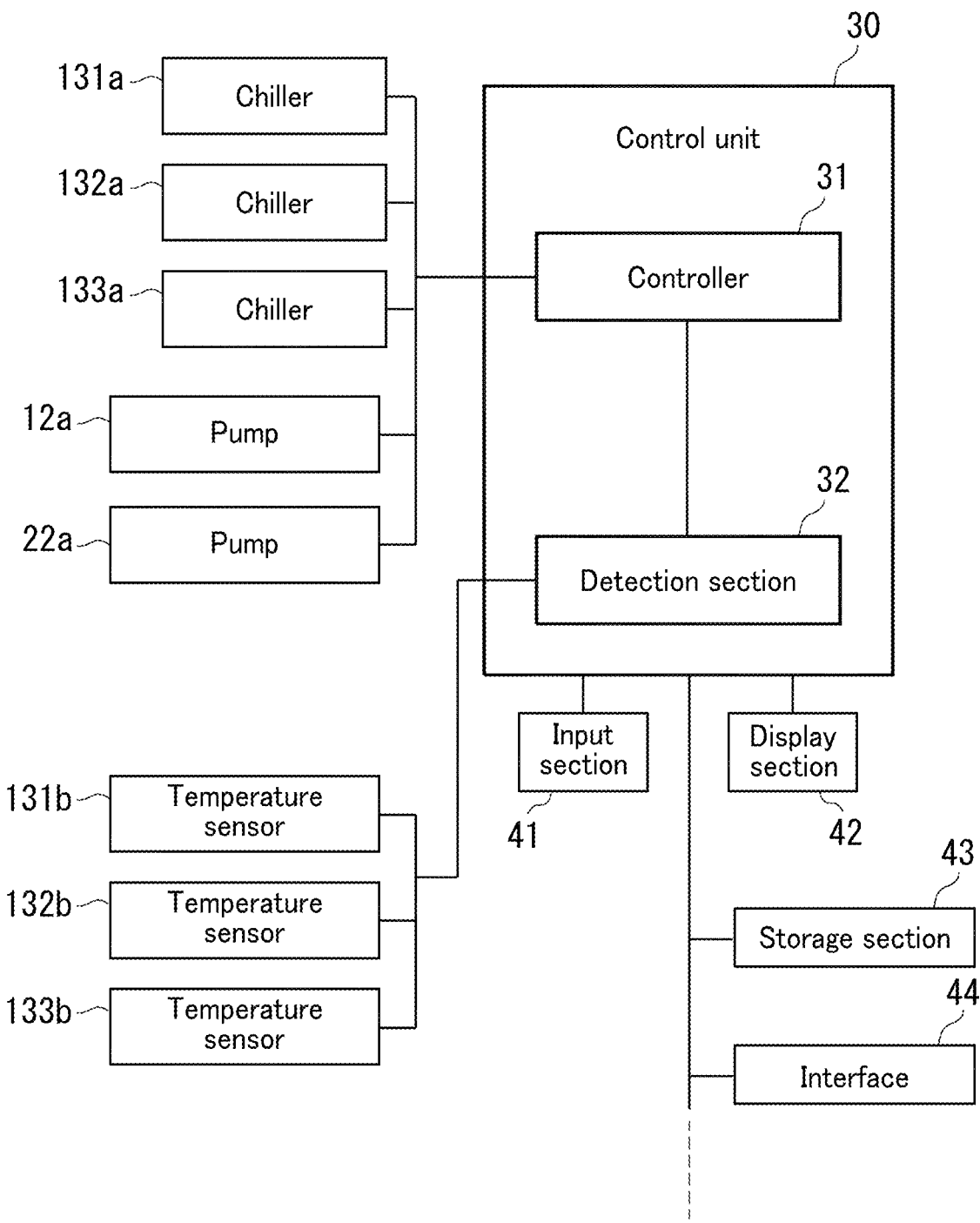
FIG. 5 is a block diagram illustrating function by function configuration of a control unit of an apparatus for controlling a concentration of a dialysis target according to the embodiment of the present invention.

The liposome producing apparatus 10 (dialyzer) according to the present embodiment incudes a control unit 30 as illustrated in FIG. 5. The following describes configuration of the control unit 30 with reference mainly to FIG. 5.

As illustrated in FIG. 5, the control unit 30 includes a controller 31 and a detection section 32. The controller 31 and the detection section 32 are connected together in a communicable manner.

The controller 31 is constituted by a CPU (central processing unit), a ROM (read only memory), a RAM (random access memory), and drive circuits for various types of actuators included in the liposome producing apparatus 10. The ROM 52 stores therein various types of programs such as a BIOS (basic input/output system), an OS (operation system), various types of drivers, and various types of applications. The detection section 32 is constituted by detection circuits of various sensors (for example, temperature sensors 131b, 132b, and 133b) included in the liposome producing apparatus 10.

The control unit 30 is connected to an input section 41, a display section 42, a storage section 43, and an interface 44 in a communicable manner. The interface 44 enables data sending and receiving between the control unit 30 and an external device. The control unit 30 is connected to for example a general-purpose computer (so-called a personal computer) via the interface 44.

The input section 41 receives input from a user. The input section 41 is constituted by for example a key board, a mouse, or a touch panel. The display section 42 is constituted by a display such as a liquid crystal display (LCD) or an electroluminescence display (ELD). Note that in a configuration in which the input section 41 and the display section 42 are constituted by a touch panel, the input section 41 and the display section 42 are unified.

The storage section 43 is constituted by for example a non-volatile memory such as hard disk. The storage section 43 stores therein for example programs for various controls and data (for example, data input from the input section 41 to the control unit 30).

The controller 31 controls the pumps 12a and 22a based on data input from the input section 41 to the control unit 30. The controller 31 further controls the chillers 131a, 132a, and 133a based on output signals from the respective temperature sensors 131b, 132b, and 133b input to the detection section 32 and data or a command input from the input section 41 to the control unit 30.

The control unit 30 of the liposome producing apparatus 10 according to the present embodiment controls a concentration of the dialysis target (liposome liquid 11b after dialysis) flowing out of the outlet 20b of the first flow channels 201 based on a difference between a flow rate of the dialysis target (liposome liquid 11b before dialysis) at the inlet 20a of the first flow channels 201 (hereinafter referred to as a first flow rate) and a flow rate of the dialysis target (liposome liquid after dialysis) at the outlet 20b of the first flow channels 201 (hereinafter referred to as a second flow rate). Note that the difference between the first and second flow rates can be expressed by a value obtained by subtracting one of the first and second flow rates from the other flow rate or a value obtained by dividing one of the first and second flow rates by the other flow rate. The concentration of the dialysis target corresponds to a ratio of a specific particles (for example, the liposomes 101) to the dialysis target (for example, the liposome liquid 11b). Control of the concentration of the dialysis target as above will be described below with reference mainly to FIGS. 6 and 7.

Control on for example the pump 12a (FIG. 1) by the control unit 30 (FIG. 5) can set the first flow rate to a predetermined rate. Also, control on for example the pump 16a by the controller 31 can set the second flow rate to a predetermined rate.

Changing for example the second flow rate while keeping the first flow rate can change a ratio of the second flow rate to the first flow rate (second flow rate/first flow rate). Hereafter, the ratio of the second flow rate to the first flow rate (second flow rate/first flow rate) will be referred to as a flow rate ratio between before and after dialysis.

Figure 6:
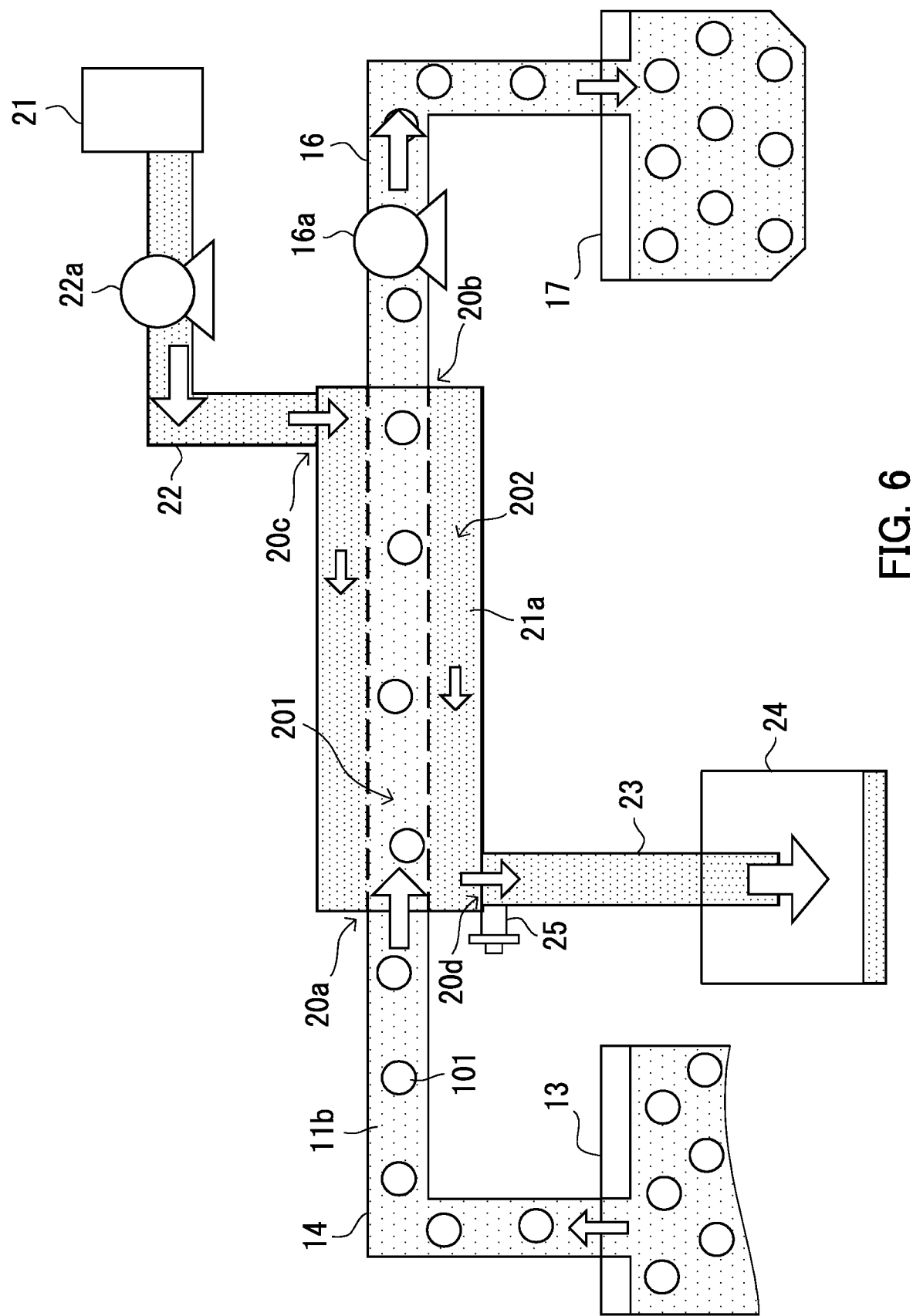
FIG. 6 is a diagram explaining control in a situation in which organic particulates in a dialysis target (liposome liquid) are removed without substantially changing the concentration of the dialysis target.

Setting the flow rate ratio between before and after dialysis for example to 1.0 (first flow rate=second flow rate) can result in removal of the organic particulates 103 (FIG. 4) in the liposome liquid 11b without substantially changing the concentration of the liposome liquid 11b, as illustrated in FIG. 6. During the liposome liquid 11b flowing in the first flow channels 201, an amount of the dispersion medium 102 traveling from the first flow channels 201 to the second flow channel 202 is substantially equal to an amount of the dispersion medium 102 traveling from the second flow channel 202 to the first flow channels 201.

Figure 7:
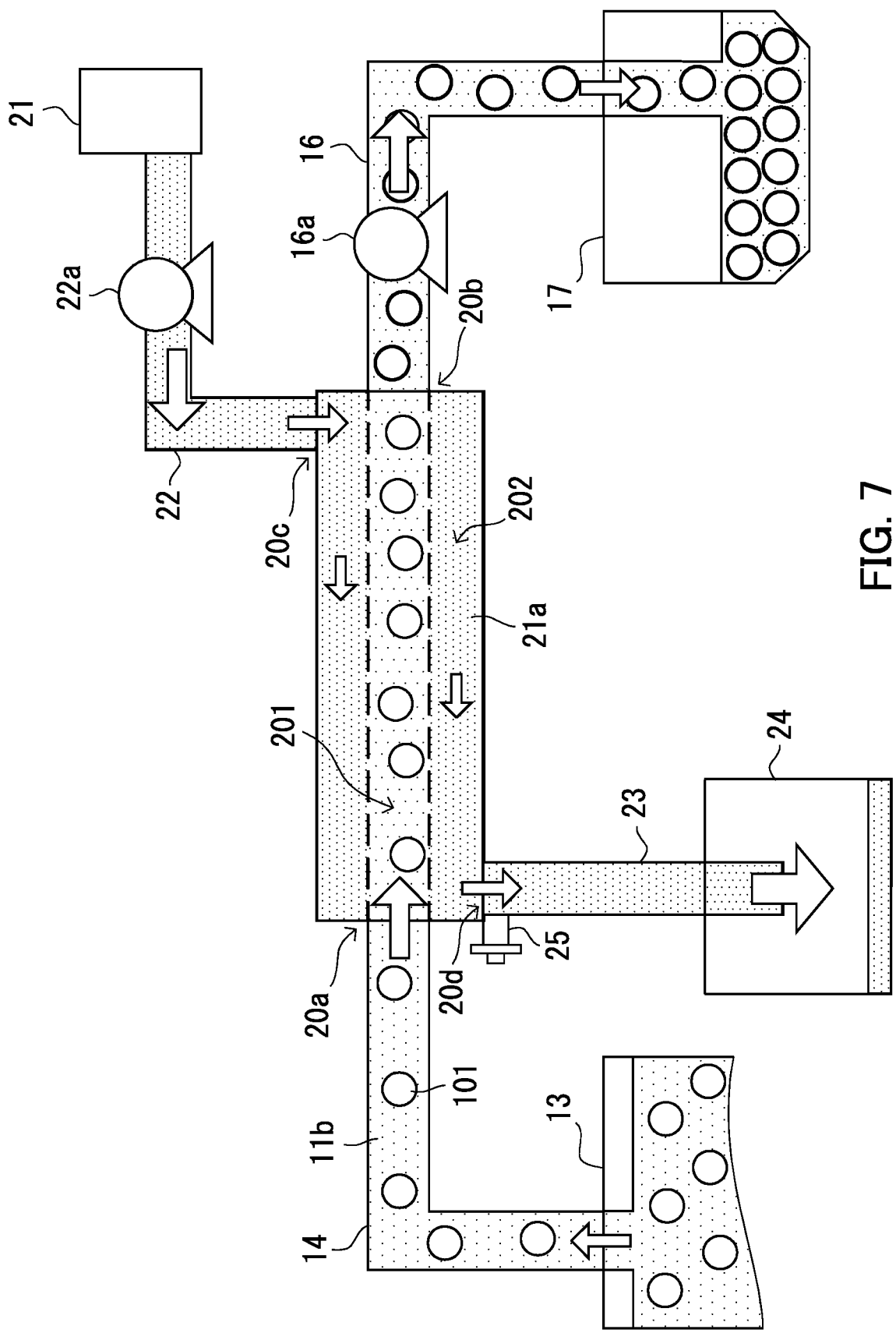
FIG. 7 is a diagram explaining control in a situation in which the dialysis target (liposome liquid) is condensed while organic particulates are removed.

Furthermore, setting the flow rate ratio between before and after dialysis for example smaller than 1.0 (first flow rate>second flow rate) can result in condensation of the liposome liquid 11b in parallel to removal of the organic particulates 103 (FIG. 4) in the liposome liquid 11b, as illustrated in FIG. 7. Specifically, when the first flow rate is set higher than the second flow rate, an amount of liquid flowing in the inlet 20a of the first flow channels 201 is smaller than an amount of liquid flowing out of the outlet 20b of the first flow channels 201. Further, the dispersion medium 102 in the liposome liquid 11b flowing in the first flow channels 201 travels from the first flow channels 201 to the second flow channel 202 in a manner to pass through the pores of the hollow fiber membranes 201a. The liposomes 101, which are larger than the pores 201b (FIG. 4) of the hollow fiber membranes 201a, do not travel from the first flow channels 201 to the second flow channel 202. The concentration of the liposome liquid at the liposome liquid 11b flowing out of the outlet 20b of the first flow channels 201 is accordingly higher than the concentration of the liposome liquid at the liposome liquid 11b flowing into the inlet 20a of the first flow channels 201.

Moreover, when the flow rate ratio between before and after dialysis is set larger than 1.0 (first flow rate<second flow rate), the dispersion medium 102 in the liposome liquid 11b travels in a direction opposite to that when the liposome liquid 11b is condensed (an example illustrated in FIG. 7). As such, when the flow rate ratio between before and after dialysis is set larger than 1.0, the liposome liquid 11b can be diluted while the organic particulates 103 in the liposome liquid 11b can be removed.

Note that the concentration of the dialysis target (liposome liquid 11b after dialysis) is controlled by controlling the ratio of the second flow rate to the first flow rate (second flow rate/first flow rate) in the above example. However, the concentration of the dialysis target (liposome liquid 11b after dialysis) may be controlled by controlling a ratio of the first flow rate to the second flow rate (first flow rate/second flow rate). Alternatively, the concentration of the dialysis target (liposome liquid 11b after dialysis) may be controlled by controlling a value obtained by subtracting one of the first and second flow rates from the other flow rate (first flow rate−second flow rate or second flow rate−first flow rate).

As described above, the dialyzer (the purification section 15 and the like) according to the present embodiment includes the hollow fiber dialysis column 20, the pump 12a (liquid tubing section), and the pump 16a (flow rate changing section). The hollow fiber dialysis column 20 includes the hollow fiber membranes 201a, the first flow channels 201 that allow the dialysis target to flow internally of the hollow fiber membranes 201a, and the second flow channel 202 that allows the external liquid 21a to flow externally of the hollow fiber membranes 201a. The pump 12a is disposed upstream of the inlet 20a of the first flow channels 201. The pump 12a sends the dialysis target to the first flow channels 201 at a predetermined flow rate. The pump 16a is disposed downstream of the outlet 20b of the first flow channels 201. The pump 16a is capable of changing the flow rate of the dialysis target at the dialysis target flowing out of the outlet 20b of the first flow channels 201. The pump 16a sends the dialysis target flowing out of the outlet 20b of the first flow channels 201 at a predetermined flow rate.

Furthermore, the apparatus for controlling a concentration of a dialysis target according to the present embodiment includes the control unit 30. The control unit 30 causes the dialysis target to flow in the first flow channels 201 and the external liquid 21a to flow in the second flow channel 202 and controls the concentration of the dialysis target flowing out of the outlet 20b of the first flow channels 201 based on the flow rate ratio between before and after dialysis (ratio between a flow rate of the dialysis target at the inlet 20a of the first flow channels 201 and a flow rate of the dialysis target at the outlet 20b of the first flow channels 201). Specifically, the control unit 30 controls for example the pump 16a (more specifically, a flow rate at which the pump 16a tubes liquid per unit time). Note that the above control may be executed by only hardware (for example, a dedicated circuit) or by causing the CPU to execute programs.

In order to condense the dialysis target, the control unit 30 sets the concentration of the dialysis target at the outlet 20b of the first flow channels 201 lower than that at the inlet 20a of the first flow channels 201 by setting the flow rate of the dialysis target at the outlet 20b of the first flow channels 201 higher than that at the inlet 20a of the first flow channels 201. By contrast, in order to dilute the dialysis target, the control unit 30 sets the concentration of the dialysis target at the outlet 20b of the first flow channels 201 higher than that at the inlet 20a of the first flow channels 201 by setting the flow rate of the dialysis target at the outlet 20b of the first flow channels 201 lower than that at the inlet 20a of the first flow channels 201.

According to the dialyzer (the purification section 15 and the like) of the present embodiment, the concentration of the dialysis target flowing out of the hollow fiber dialysis column 20 can be easily controlled by controlling the pump 16a by the control unit 30. As a result, a dialysis target having a desired concentration can be yielded with high precision.

Figure 8:
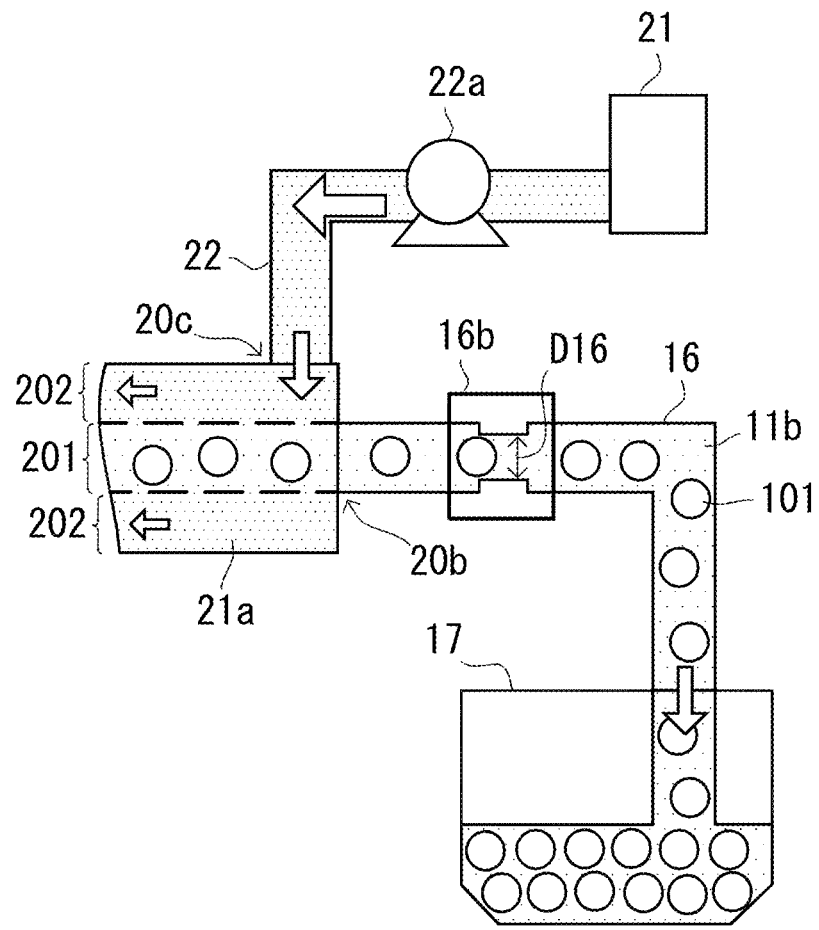
FIG. 8 is a diagram illustrating a variation of a flow rate changing section of the dialyzer according to the embodiment of the present invention.

The flow rate changing section capable of changing the flow rate of the dialysis target at the dialysis target flowing out of the outlet 20b of the first flow channels 201 is not limited to the pump 16a and may be any device. The flow rate changing section may be for example a flow channel area changing device 16b (for example, a throttle) as illustrated in FIG. 8 in place of the pump 16a. The flow channel area changing device 16b has a flow channel of which flow channel width D16 (eventually, a flow channel area) is changeable. A side wall of the flow channel is for example shifted inward or outward to change the flow channel width D16 (flow channel area). The flow channel area changing device 16b can be disposed for example at the tube 16 (particularly, in a vicinity of the outlet 20b of the first flow channels 201). The flow rate of the dialysis target at the dialysis target flowing out of the outlet 20b of the first flow channels 201 can be reduced by reducing the flow channel width D16 (eventually, flow channel area).

It is preferable that the control unit 30 can control the flow channel area changing device 16b (for example, the flow channel width D16).

The control unit 30 in the present embodiment controls the concentration of the dialysis target flowing out of the outlet 20b of the first flow channels 201 by changing the flow rate of the dialysis target at the outlet 20b of the first flow channels 201 while keeping the flow rate of the dialysis target at the inlet 20a of the first flow channels 201 constant. In the apparatus for controlling a concentration of a dialysis target having the above configuration, the concentration of the dialysis target flowing out of the hollow fiber dialysis column 20 can be easily controlled with high precision.

However, the configuration is not limited to the above. The concentration of the dialysis target flowing out of the outlet 20b of the first flow channels 201 may be controlled by changing both the first flow rate (flow rate of the dialysis target at the inlet 20a of the first flow channels 201) and the second flow rate (flow rate of the dialysis target at the outlet 20b of the first flow channels 201).

The control unit 30 in the present embodiment controls the concentration of the dialysis target in a state in which a flow rate of the external liquid 21a at the inlet 20c of the second flow channel 202 (hereinafter referred to as a third flow rate) is higher than the second flow rate (flow rate of the dialysis target at the outlet 20b of the first flow channels 201). The third flow rate is preferably higher than the second flow rate in adjustment of a concentration of the dialysis target. Specifically, the third flow rate is preferably at least 10 times and no greater than 100 times the second flow rate and more preferably at least 30 times and no greater than 80 times the second flow rate. Setting the third flow rate higher than the second flow rate can achieve favorable control of the concentration of the dialysis target based on the flow rate ratio between before and after dialysis. The higher the third flow rate is, the more dialysis efficiency tends to increase.

The liposome liquid 11b (dialysis target) in the first flow channels 201 flows in a direction opposite to a direction in which the external liquid 21a flows in the second flow channel 202 in the dialyzer (the purification section 15 and the like) according to the present embodiment. Dialysis efficiency can increase in the dialyzer having the above configuration.

The production section 13, the purification section 15, and the collection section 17 (i.e., a system in which the dialysis target flows) are connected together in a sealed manner in the liposome producing apparatus 10 according to the present embodiment. In the above configuration, production, purification, and collection of the liposome liquid 11b (liposomes 101) can be performed in a sealed space continuously (eventually, in a series of processing). Through the above, invasion of fungus from outside can be prevented. Therefore, the liposome producing apparatus 10 (dialyzer) according to the present embodiment is suitable for drug production. The liposome producing apparatus 10 according to the present embodiment is particularly suitable for production of liposomes that each encapsulate a composition of a therapeutic medicine for inflammatory disease. Note that a system in which the external liquid 21a flows (particularly, a downstream part thereof) need not be necessarily sealed.

The liposome liquid 11b (dialysis target) passes through the first flow channels 201 from the inlet 20a to the outlet 20b thereof only one time in the liposome producing apparatus 10 according to the present embodiment. By not circulating the liposome liquid 11b, concentration adjustment is enabled more efficiently and the liposome liquid 11b (dialysis target) can be dialyzed more efficiently than in a configuration in which the liposome liquid 11b is circulated. Moreover, the configuration of the liposome producing apparatus 10 can be simplified, thereby achieving easy maintenance of the sealed space. However, the configuration is not limited to the above. The liposome liquid 11b (dialysis target) may be allowed to pass through the first flow channels 201 from the inlet 20a to the outlet 20b thereof plural times (the liposome liquid 11b is circulated) for further dialysis of the liposome liquid 11b (dialysis target) and concentration adjustment (condensation or dilution).

When a concentration of the produced liposome liquid is too high, preservation stability of the liposome liquid may be impaired. According to the liposome producing apparatus 10 of the present embodiment, a liposome liquid at a desired concentration can be easily yielded. In a situation in which the concentration of a dialysis target (for example, a liposome liquid) is adjusted, the flow rate ratio between before and after dialysis is preferably set to at least 0.2 and no greater than 5.0 and more preferably at least 0.5 and no greater than 2.0. Setting the flow rate ratio between before and after dialysis to at least 0.2 and no greater than 5.0 (preferably at least 0.5 and no greater than 2.0) can result in adjustment of the concentration of the dialysis target with high precision.

In the method for controlling a concentration of a dialysis target according to the present embodiment, the concentration of the dialysis target flowing out of the outlet 20b of the first flow channels 201 is controlled by controlling at least one of an amount of liquid traveling from the first flow channels 201 to the second flow channel 202 and an amount of liquid traveling from the second flow channel 202 to the first flow channels 201 while causing the dialysis target to flow in the first flow channels 201 and the external liquid 21a to flow in the second flow channel 202 for dialysis of the dialysis target. According to the method for controlling a concentration of a dialysis target of the present embodiment, the concentration of the dialysis target can be easily controlled using the hollow fiber dialysis column 20.

A difference between the amount of liquid traveling from the first flow channels 201 to the second flow channel 202 and the amount of liquid traveling from the second flow channel 202 to the first flow channels 201 can be favorably controlled by controlling a difference between the flow rate of the dialysis target at the inlet of the first flow channels 201 and the flow rate of the dialysis target at the outlet of the first flow channels 201.

Any manner to place the hollow fiber dialysis column 20 (posture in dialysis) is adoptable. For example, the hollow fiber dialysis column 20 may be placed vertically (in a posture in which a longitudinal direction of the column is parallel to a vertical line) or horizontally (in a posture in which the longitudinal direction of the column is parallel to a horizontal plane). However, in a configuration in which the hollow fiber dialysis column 20 is placed horizontally, the concentration of the dialysis target can be easily controlled. The reason therefor is thought to be gravity being uniformly applied to the entire hollow fiber dialysis column 20.

When the inner diameters of the respective hollow fiber membranes 201a (inner diameters of the respective fibers) D13 (FIG. 4) are increased or a plurality of hollow fiber dialysis columns are connected in parallel, an amount of liquid in treatment (dialysis or concentration adjustment) per one time can be increased. Alternatively, the amount of liquid in treatment may be increased by increasing the flow rate of the dialysis target at the inlet 20a of the first flow channels 201. In the above methods, the amount of liquid in treatment can be increased easily only by flow rate adjustment. However, a too high flow rate of the dialysis target at the inlet 20a of the first flow channels 201 may tend to reduce dialysis efficiency. Even in a situation in which dialysis efficiency reduces, sufficient dialysis can be performed by increasing the number of hollow fiber dialysis columns connected in series.

EXAMPLES

First Example

Description will be made below with reference mainly to FIGS. 9 and 10 about an experiment (first example) in which a concentration of a dialysis target is controlled by actually using the liposome producing apparatus 10 illustrated in FIG. 1.

[Experiment Apparatus]

A apparatus used in the experiment will be described first.

A liposome continuous production apparatus ("Lipo-TB" manufactured by Toray Engineering Co., Ltd.) was used as a combination of the raw material supply section 10a and the production section 13. The pump 12a was a valveless metering pump ("RH-OCTC-LF" manufactured by Fluid Metering, Inc.). The tube 12 was a tube made of thermoplastic elastomer-based plastic and having an inner diameter of 0.8 mm. A vessel made of borosilicate glass was used as the vessel 11.

Two columns that each were "MidiKros (registered Japanese trademark) module" manufactured by Spectrum Laboratories, Inc. were used as the hollow fiber dialysis column 20. Specifically, two hollow fiber dialysis columns (each were MidiKros module) were connected together in a longitudinal direction (in series) to form the hollow fiber dialysis column 20 that was substantially long. In each of the two hollow fiber dialysis columns (each were MidiKros module), the hollow fiber membranes 201a each had a surface area of 370 cm$^2$ and a molecular weight cut off (MWCO) of 500 kD and the first flow channels 201 each had a length of 70 cm. In a configuration in which the two hollow fiber dialysis columns were connected together, a length D11 (FIG. 1) of the first flow channels 201 from the inlet 20a to the outlet 20b was 140 cm. The hollow fiber dialysis column 20 was placed horizontally.

A vessel made of polyethylene was used as the vessel 21. A peristaltic pump ("KrosFlo (registered Japanese trademark) Research IIi pump" manufactured by Spectrum Laboratories, Inc.) was used as the pump 22a. A vessel made of polyethylene was used as the waste liquid container 24.

A peristaltic pump ("ISM597D" manufactured by ISMATEC) was used as the pump 16a. A tube made of thermoplastic elastomer-based plastic and having an inner diameter of 0.8 mm was used as each of the tubes 14 and 16. The tube 22 was a tube made of thermoplastic elastomer-based plastic and having an inner diameter of 3.1 mm. The tube 23 was a tube made of thermoplastic elastomer-based plastic and having an inner diameter of 6.4 mm. A vessel made of polypropylene was used as the collection section 17.

The waste liquid container 24 was disposed at a level 110 cm lower than (below) the hollow fiber dialysis column 20. In the first example, no filter is disposed at the outlet 20d of the second flow channel 202.

[Dialysis Target and External Liquid]

Description will be made next about a dialysis target and an external liquid 21a that were used in the experiment.

The dialysis target was a liposome liquid 11b produced by the liposome continuous production apparatus (Lipo-TB). The liposome liquid 11b contained liposomes 101, 10% by mass of a maltose solution (dispersion medium 102) containing sodium phosphate, and isopropanol (organic particulates 103). A multitude of the liposomes 101 were dispersed in the dispersion medium 102 of the liposome liquid 11b. Cyclosporine (the drug 101e) was encapsulated in each of the liposomes 101, as illustrated for example in FIG. 3B. A concentration of cyclosporine in the raw material 11a was 1.00 mg/mL. A concentration of isopropanol in the raw material 11a was 16.6% by mass. Further, surfaces of the respective liposomes 101 were modified by PEG (the modifier 101d). The liposomes 101 had an average particle diameter D12 of at least 93 nm and no greater than 101 nm.

In addition, the external liquid 21a was 10% by mass of the maltose solution containing sodium phosphate.

[Evaluation Method and Evaluation Results]

The liposome liquid 11b produced by the liposome continuous production apparatus (Lipo-TB) was dialyzed using the hollow fiber dialysis column 20 in the experiment. Production and dialysis were performed in series. In the dialysis, the liposome liquid 11b was allowed to pass through the first flow channels 201 from the inlet 20a to the outlet 20b thereof only one time. In so doing, a flow rate of the dialysis target at the outlet 20b of the first flow channels 201 (flow rate at a column outlet) was changed while a flow rate of the dialysis target at the inlet 20a of the first flow channels 201 (flow rate at a column inlet) was kept constant (2.00 mL/min.). Specifically, the flow rate at the column outlet was changed by changing the setting value of a flow rate of the pump 16a. FIG. 9 indicates experiment conditions (conditions 1-1 to 1-3) and experiment results (concentration of the liposome liquid 11b).

As indicated in FIG. 9, the liposome liquid 11b was dialyzed under the respective conditions 1-1 to 1-3 (three types of flow rate ratios or condensation ratios between before and after dialysis) and the concentration of cyclosporine contained in the liposome liquid after dialysis was measured. Note that a flow rate of the external liquid 21a at the inlet 20c of the second flow channel 202 (flow rate of the external liquid) was 60.0 mL/min. in any of the conditions 1-1 to 1-3.

In the conditions 1-1, the flow rate at the column inlet was 2.00 mL/min. and the flow rate at the column outlet was 2.00 mL/min. The condensation ratio between before and after dialysis in the conditions 1-1 (flow rate at column inlet/flow rate at column outlet) was 1.000 (=2.00/2.00). In the conditions 1-2, the flow rate at the column inlet was 2.00 mL/min. and the flow rate at the column outlet was 1.33 mL/min. The condensation ratio between before and after dialysis in the conditions 1-2 was 1.504 (≅2.00/1.33). In the conditions 1-3, the flow rate at the column inlet was 2.00 mL/min. and the flow rate at the column outlet was 3.00 mL/min. The condensation ratio between before and after dialysis in the conditions 1-3 was 0.667 (≅2.00/3.00).

In the dialysis of the liposome liquid 11b under the conditions 1-1, the concentration of cyclosporine after dialysis was 1.135 mg/mL.

In the dialysis of the liposome liquid 11b under the conditions 1-2, the concentration of cyclosporine after dialysis was 1.661 mg/mL. The liposome liquid 11b was condensed in the course of the dialysis.

In the dialysis of the liposome liquid 11b under the conditions 1-3, the concentration of cyclosporine after dialysis was 0.770 mg/mL. The liposome liquid 11b was diluted in the course of the dialysis.

Note that the concentration of isopropanol contained in the liposome liquid 11b was reduced to 1.0% by mass or less through the dialysis under any of the conditions 1-1 to 1-3. A time taken for each dialysis (time taken for the liposome liquid 11b to pass through the hollow fiber dialysis column 20) was about ten minutes.

Figure 10:
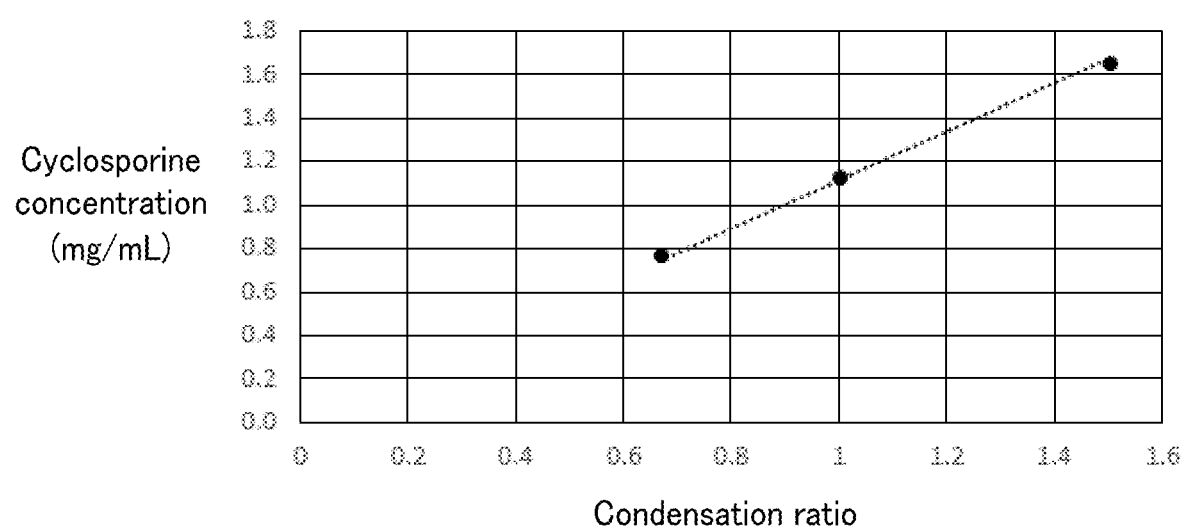
FIG. 10 is a graph representation indicating a correlation between concentration of cyclosporine and a condensation ratio between before and after dialysis in the first example of the present invention.

FIG. 10 is a graph representation indicating a correlation between the condensation ratio between before and after dialysis and the concentration of cyclosporine after dialysis among experimental data listed in FIG. 9.

As indicated in FIG. 10, a highly precise proportional relationship (linear relationship) existed between the condensation ratio between before and after dialysis (flow rate at column inlet/flow rate at column outlet) and the concentration of cyclosporine in a state in which the flow rate at the column inlet was kept constant (2.00 mL/min.). The relationship between the condensation ratio (x) and the concentration of cyclosporine (y) can be represented by an expression "y=1.1187x" wherein a coefficient of determination $R^2$ was 0.9968. As such, the liposome liquid 11b having a desired concentration could be yielded easily by controlling the flow rate at the column outlet (the pump 16a).

Second Example

Description will be made below with reference mainly to FIG. 11 about an experiment (second example) in which a concentration of a dialysis target was controlled by actually using the liposome producing apparatus 10 illustrated in FIG. 1. Note that the second example was carried out under the same conditions as those in the first example other than the followings.

As listed in FIG. 11, the liposome liquid 11b was dialyzed under respective conditions 2-1 and 2-2 (two types of flow rates of the external liquid) and a concentration of isopropanol contained in the liposome liquid after dialysis was measured. Note that a flow rate of the dialysis target at the inlet 20a of the first flow channels 201 (flow rate at a column inlet) was 2.00 mL/min. and a flow rate of the dialysis target at the outlet 20b of the first flow channels 201 (flow rate at a column outlet) was 2.00 mL/min. in either of the conditions 2-1 and 2-2.

A flow rate of the external liquid 21a at the inlet 20c of the second flow channel 202 (flow rate of the external liquid) in the conditions 2-1 was 40.0 mL/min. A flow rate of the external liquid 21a in the conditions 2-1 (40.0 mL/min.) was 20 times the flow rate at the column outlet (2.00 mL/min.). A flow rate of the external liquid 21a at the inlet 20c of the second flow channel 202 (flow rate of the external liquid) in the conditions 2-2 was 60.0 mL/min. The flow rate of the external liquid (60.0 mL/min.) was 30 times the flow rate at the column outlet (2.00 mL/min.) in the conditions 2-2.

A concentration of isopropanol after dialysis was 0.79% by mass when the liposome liquid 11b was dialyzed under the conditions 2-1.

A concentration of isopropanol after dialysis was 0.36% by mass when the liposome liquid 11b was dialyzed under the conditions 2-2.

Dialysis efficiency increased by increasing the flow rate of the external liquid in the above experiment. The reason therefor is inferred to be respective increases in amount of liquid traveling from the first flow channels 201 to the second flow channel 202 and amount of liquid traveling from the second flow channel 202 to the first flow channels 201.

Third Example

Description will be made below with reference mainly to FIGS. 12A and 12B about an experiment (third example) in which a concentration of a dialysis target was controlled by actually using the liposome producing apparatus 10 illustrated in FIG. 1. Note that the third example was carried out under the same conditions as those in the first example other than the followings.

Pressure sensors ("ACPM-799-01S" manufactured by Spectrum Laboratories, Inc.) each for detecting an internal pressure of a tube were disposed at the inlet 20a and the outlet 20b of the first flow channels 201 and the inlet 20c and the outlet 20d of the second flow channel 202.

As indicated in FIG. 12A, the liposome liquid 11b was dialyzed under respective conditions 3-1 and 3-2 (two types of positions of the waste liquid container) and a concentration of isopropanol contained in the liposome liquid after dialysis was measured. Note that a flow rate of the dialysis target at the inlet 20a of the first flow channels 201 (flow rate at a column inlet) was 2.00 mL/min. and a flow rate of the dialysis target at the outlet 20b of the first flow channels 201 (flow rate at a column outlet) was 2.00 mL/min. in the respective conditions 3-1 and 3-2.

The waste liquid container 24 was disposed at a level 110 cm lower than (below) the hollow fiber dialysis column 20 in the conditions 3-1. The waste liquid container 24 was disposed at the same level as the hollow fiber dialysis column 20 in the conditions 3-2.

The concentration of isopropanol after dialysis was 0.36% by mass when the liposome liquid 11b was dialyzed under the conditions 3-1.

The concentration of isopropanol after dialysis was 0.58% by mass when the liposome liquid 11b was dialyzed under the conditions 3-2.

Furthermore, as indicated in FIG. 12B, the above pressure sensors measured pressures at the respective inlets and the respective outlets of the first and second flow channels 201 and 202 (inlet 20a, outlet 20b, inlet 20c, and outlet 20d) during the dialysis under the respective conditions 3-1 and 3-2 in the present experiment. In the above pressure measurement, a zero point (reference) was determined to be a pressure in a state in which the hollow fiber dialysis column 20 was filled with liquid while liquid in the tube 23 (drain tube) was removed.

During the dialysis under the conditions 3-1, the pressure at the inlet 20a of the first flow channels 201 (pressure at an internal flow channel inlet) was 15 mb (1,500 Pa) and the pressure at the outlet 20b of the first flow channels 201 (pressure at an internal flow channel outlet) was −4 mb (−400 Pa). Also, the pressure at the inlet 20c of the second flow channel 202 (pressure at an external flow channel inlet) was 12 mb (1,200 Pa) and the pressure at the outlet 20d of the second flow channel 202 (pressure at an external flow channel outlet) was −41 mb (−4,100 Pa).

During the dialysis under the conditions 3-2, the pressure at the inlet 20a of the first flow channels 201 (pressure at the internal flow channel inlet) was 97 mb (9,700 Pa) and the pressure at the outlet 20b of the first flow channels 201 (pressure at the internal flow channel outlet) was 75 mb (7,500 Pa). Also, the pressure at the inlet 20c of the second flow channel 202 (pressure at the external flow channel inlet) was 88 mb (8,800 Pa) and the pressure at the outlet 20d of the second flow channel 202 (pressure at the external flow channel outlet) was 35 mb (3,500 Pa).

Dialysis efficiency increased when the waste liquid container 24 was disposed at a lower level than the hollow fiber dialysis column 20 in the above experiment. The reason therefor is inferred to be that when the waste liquid container 24 is disposed lower (in the gravity direction) than the hollow fiber dialysis column 20, the external liquid 21a easily flows out of the hollow fiber dialysis column 20.

Fourth Example

Description will be made below with reference mainly to FIGS. 13A and 13B about an experiment (fourth example) in which a concentration of a dialysis target was controlled by actually using the liposome producing apparatus 10 illustrated in FIG. 1. Note that the fourth example was carried out under the same conditions as those in the first example other than the followings.

Pressure sensors ("ACPM-799-01S" manufactured by Spectrum Laboratories, Inc.) each for detecting an internal pressure of a tube were disposed at the inlet 20a and the outlet 20b of the first flow channels 201 and the inlet 20c and the outlet 20d of the second flow channel 202.

As indicated in FIG. 13A, the liposome liquid 11b was dialyzed under respective conditions 4-1 and 4-2 (two types of positions of the waste liquid container) and a concentration of isopropanol contained in the liposome liquid after dialysis was measured. Note that the flow rate of the dialysis target at the inlet 20a of the first flow channels 201 (flow rate at a column inlet) was 2.00 mL/min. and the flow rate of the dialysis target at the outlet 20b of the first flow channels 201 (flow rate at a column outlet) was 2.00 mL/min. in the respective conditions 4-1 and 4-2.

No filter was disposed at the outlet 20d of the second flow channel 202 (a joint part between the hollow fiber dialysis column 20 and the tube 23) in the conditions 4-1. A filter ("Millex-FG50" manufactured by Merck Millipore Corporation) was deposed at the outlet 20d of the second flow channel 202 in the conditions 4-2.

The concentration of isopropanol after dialysis was 0.36% by mass when the liposome liquid 11b was dialyzed under the conditions 4-1.

The concentration of isopropanol after dialysis was 0.28% by mass when the liposome liquid 11b was dialyzed under the conditions 4-2.

Furthermore, as indicated in FIG. 13B, the pressure sensors measured pressures at the respective inlets and the respective outlets of the first and second flow channels 201 and 202 (the inlet 20a, the outlet 20b, the inlet 20c, and the outlet 20d) under the respective conditions 4-1 and 4-2 in the present experiment. In the above pressure measurement, a zero point (reference) was determined to be a pressure in a state in which the hollow fiber dialysis column 20 was filled with liquid and liquid in the tube 23 (drain tube) was removed.

During the dialysis under the conditions 4-1, the pressure at the inlet 20a of the first flow channels 201 (pressure at an internal flow channel inlet) was 15 mb (1,500 Pa) and the pressure at the outlet 20b of the first flow channels 201 (pressure at an internal flow channel outlet) was −4 mb (−400 Pa). Also, the pressure at the inlet 20c of the second flow channel 202 (pressure at an external flow channel inlet) was 12 mb (1,200 Pa) and the pressure at the outlet 20d of the second flow channel 202 (pressure at an external flow channel outlet) was −41 mb (−4,100 Pa).

During the dialysis under the conditions 4-2, the pressure at the inlet 20a of the first flow channels 201 (pressure at the internal flow channel inlet) was 59 mb (5,900 Pa) and the pressure at the outlet 20b of the first flow channels 201 (pressure at the internal flow channel outlet) was 41 mb (4,100 Pa). Also, the pressure at the inlet 20c of the second flow channel 202 (pressure at the external flow channel inlet) was 57 mb (5,700 Pa) and the pressure at the outlet 20d of the second flow channel 202 (pressure at the external flow channel outlet) was 1 mb (100 Pa).

As indicated in FIG. 13A, dialysis efficiency increased when the waste liquid container 24 was disposed at a lower level than (below) the hollow fiber dialysis column 20 and the filter was disposed at the outlet 20d of the second flow channel 202 (a joint part between the hollow fiber dialysis column 20 and the tube 23) in the above experiment. Furthermore, as indicated in FIG. 13B, when no filter was provided at the outlet 20d of the second flow channel 202 (in the conditions 4-1) in a configuration in which the waste liquid container 24 was disposed at a lower level than the hollow fiber dialysis column 20, negative pressure was applied to the hollow fiber dialysis column 20 (pressure at the external flow channel outlet and pressure at the internal flow channel outlet each were a negative value) to reduce an internal pressure of the hollow fiber dialysis column 20. By contrast, when the filter is disposed at the outlet 20$d$ of the second flow channel 202 (under the conditions 4-2) in a configuration in which the filter is provided at the outlet 20$d$ of the second flow channel 202, no negative pressure was applied to the hollow fiber dialysis column 20 (pressure at the external flow channel outlet and pressure at the internal flow channel outlet each were a positive value) to increase the internal pressure of the hollow fiber dialysis column 20. It is inferred that increased internal pressure of the hollow fiber dialysis column 20 increased dialysis efficiency in the conditions 4-2.

Another Example

When the flow rate of a dialysis target at the inlet 20$a$ of the first flow channels 201 was set within a range of 3 mL/min. to 4 mL/min. and four hollow fiber dialysis column (each were MidiKros module) were connected together in a longitudinal direction (in series), about 4 L of the dialysis target (liposome liquid) could be treated (dialyzed and condensed) over about 20 hours.

The present invention is not limited to the embodiment and the examples described above. The following variations are possible for example in practice.

A pump for controlling the flow rate of the dialysis target at the inlet 20$a$ of the first flow channels 201 (for example, for keeping the flow rate constant) may be disposed between the production section 13 and the purification section 15.

A flow rate sensor may be provided in the purification section 15 for detecting at least one of the flow rate of the dialysis target at the inlet 20$a$ of the first flow channels 201, the flow rate of the dialysis target at the outlet 20$b$ of the first flow channels 201, the flow rate of the external liquid 21$a$ at the inlet 20$c$ of the second flow channel 202, and the flow rate of the external liquid 21$a$ at the outlet 20$d$ of the second flow channel 202.

The dialysis target is a liquid of any type. For example, a dispersion in which at least one of an organic compound (high molecular compound or low molecular compound), a drug, and an antibody is dispersed may be used as the dialysis target rather than the liposome liquid.

Any combination among the embodiment and the variations is possible. Selection an appropriate combination according to a purpose of use is preferable. The dialyzer may only perform removal of organic particulates (for example, a residual organic solvent or a free drug) in the dialysis target without performing liposome production.

Respective configurations (for example, configuration elements, dimensions, materials, shapes, or arrangements) of the dialyzer, the liposome producing apparatus, and the apparatus for controlling a concentration of a dialysis target in the embodiment and the examples may be altered or omitted optionally within the scope not departing from the gist of the present invention. For example, in a configuration in which sufficient dialysis efficiency can be attained, the direction in which the liposome liquid 11$b$ flows may be set to the same as the direction in which the external liquid 21$a$ flows.

INDUSTRIAL APPLICABILITY

The dialyzer, the liposome producing apparatus, and the apparatus and method for controlling a concentration of a dialysis target according to the present invention are suitable for production of for example a drug or liposomes.

REFERENCE SINGS LIST

10 liposome producing apparatus
10$a$ raw material supply section
10$b$ dialysate supply section
11 vessel
11$a$ raw material
11$b$ liposome liquid
12 tube
12$a$ pump
13 production section
14 tube
15 purification section
16 tube
16$a$ pump
16$b$ flow channel area changing device
17 collection section
20 hollow fiber dialysis column
20$a$ inlet
20$b$ outlet
20$c$ inlet
20$d$ outlet
21 vessel
21$a$ external liquid
22 tube
22$a$ pump
23 tube
24 waste liquid container
30 control unit
31 controller
32 detection section
41 input section
42 display section
43 storage section
101 interface
101 liposome
101$a$ lipid molecule
101$b$ hydrophilic portion
101$c$ hydrophobic portion
101$d$ modifier
101$e$ drug
102 dispersion medium
103 organic particulate
131-133 tank
131$b$ to 131$b$ temperature sensor
131$a$ to 133$a$ chiller
134 sterilizing filter
201 first flow channel
201$a$ hollow fiber membrane
201$b$ pore
202 second flow channel

The invention claimed is:
1. A dialyzed liposome liquid producing method comprising:
   a. providing a liposome liquid producing apparatus including a production section, a dialyzer, a collection section, a dialysate supply section, a waste liquid container, and a waste liquid treating filter;
   b. continuously producing a liposome liquid containing liposomes in the production section;
   c. dialyzing the produced liposome liquid by the dialyzer while supplying dialysate to the dialyzer by the dialysate supply section;

d. collecting the dialyzed liposome liquid in the collection section; and
e. collecting in the waste liquid container the dialysate that had passed through the dialyzer;
f. wherein the dialyzer includes:
   i. a hollow fiber dialysis column including a hollow fiber membrane, a first flow channel that has a first inlet and a first outlet and that allows a dialysis target as the liposome liquid to flow internally of the hollow fiber membrane from the first inlet to the first outlet of the first flow channel, and a second flow channel that has a second inlet and a second outlet and that allows the dialysate to flow externally of the hollow fiber membrane from the second inlet to the second outlet of the second flow channel;
   ii. a liquid tubing section configured to tube the dialysis target to the first inlet of the first flow channel; and
   iii. a flow rate changing section capable of changing a flow rate of the dialysis target at the dialysis target flowing out of the first outlet of the first flow channel,
g. the flow rate changing section is a first pump that is disposed downstream of the first outlet of the first flow channel, that is connected to the first outlet of the first flow channel through a tube, and that tubes the dialysis target flowing out of the first outlet of the first flow channel downstream at a predetermined flow rate,
   iv. the production section is connected to the first inlet via a tube,
   v. the collection section is connected to the first outlet,
   vi. the dialysate supply section is connected to the second inlet,
   vii. the waste liquid container is connected to the second outlet, and
   viii. the production section includes
      (1) a first tank in which a lipid solution is produced by dissolving a raw material in a solvent,
      (2) a second tank in which a liposome preparation liquid is produced from the lipid solution, and
      (3) a third tank for cooling the liposome preparation liquid to produce the liposome liquid,
h. the waste liquid container is connected to the second outlet of the second flow channel of the hollow fiber dialysis column through a pipe in which the dialysate flows, and is disposed at a lower level than the hollow fiber dialysis column, and
   ix. when the waste liquid treating filter is not disposed at the second outlet of the second flow channel, a negative pressure of the dialysate in the pipe is applied to the hollow fiber dialysis column to reduce an internal pressure of the hollow fiber dialysis column, where the second flow channel outlet and first flow channel outlet each have a negative pressure, and
   x. when the waste liquid treating filter is disposed at the second outlet of the second flow channel, the negative pressure of the dialysate in the pipe is released, which causes an internal pressure of the hollow fiber dialysis column to increase, thereby increasing dialysis efficiency,
i. wherein the liquid tubing section of the dialyzer is constituted by a second pump,
j. a third pump causes the dialysate to flow in the second flow channel of the hollow fiber dialysis column in the dialyzer, and
k. in the dialyzing the produced liposome liquid, the first and second pumps are controlled such that the liposome liquid flowing out of the first outlet of the first flow channel has a predetermined concentration in a state in which the second pump causes the liposome liquid to flow in the first flow channel and the third pump causes the dialysate to flow in the second flow channel.

2. The dialyzed liposome liquid producing method according to claim 1, wherein
   in the dialyzing the produced liposome liquid, a concentration of the liposome liquid at the first outlet of the first flow channel is set lower than that at the first inlet of the first flow channel by controlling the first and second pumps such that the flow rate of the liposome liquid at the first outlet of the first flow channel is higher than that at the first inlet of the first flow channel.

3. The dialyzed liposome liquid producing method according to claim 1, wherein
   in the dialyzing the produced liposome liquid, a concentration of the liposome liquid at the first outlet of the first flow channel is set higher than that at the first inlet of the first flow channel by controlling the first and second pumps such that the flow rate of the liposome liquid at the first outlet of the first flow channel is lower than that at the first inlet of the first flow channel.

4. The dialyzed liposome liquid producing method according to claim 1, wherein
   in the dialyzing the produced liposome liquid, a concentration of the liposome liquid flowing out of the first outlet of the first flow channel is controlled by changing the flow rate of the liposome liquid at the first outlet of the first flow channel by the first pump while keeping the flow rate of the liposome liquid at the first inlet of the first flow channel constant by the second pump.

5. The dialyzed liposome liquid producing method according to claim 1, wherein
   in the dialyzing the produced liposome liquid, a concentration of the liposome liquid is controlled by the first and second pumps in a state in which a flow rate of the dialysate at the second inlet of the second flow channel is higher than the flow rate of the liposome liquid at the first outlet of the first flow channel.

6. The dialyzed liposome liquid producing method according to claim 1, wherein
   in the dialyzer,
   the first outlet of the first flow channel is closer to the second inlet of the second flow channel than the first inlet of the first flow channel and the second outlet of the second flow channel, and
   the second outlet of the second flow channel is closer to the first inlet of the first flow channel than the first outlet of the first flow channel and the second inlet of the second flow channel.

7. The dialyzed liposome liquid producing method according to claim 1, wherein
   the liposome liquid producing apparatus includes a raw material supply section that supplies the raw material to the production section, and
   the raw material supply section includes
   a vessel that accommodates the raw material and the solvent,
   a connecting tube that connects the vessel to the production section, and
   a pump provided in the connecting tube.

8. The dialyzed liposome liquid producing method according to claim 1, wherein
   the liposome liquid once dialyzed is not circulated and passes through the first flow channel from the first inlet to the first outlet thereof only one time.

9. The dialyzed liposome liquid producing method according to claim 1, wherein
a flow in the first flow channel is counterflow against a flow in the second flow channel.

10. The dialyzed liposome liquid producing method according to claim 1, wherein
the waste liquid container is disposed at a lower level than the hollow fiber dialysis column.

11. The dialyzed liposome liquid producing method according to claim 1, wherein
the hollow fiber membrane has pores with a diameter of at least 2 nm and no greater than 75 nm.

12. The dialyzed liposome liquid producing method according to claim 1, wherein
the hollow fiber membrane has pores that do not allow some of the liposomes in the liposome liquid flowing from the first inlet of the first flow channel to pass therethrough.

* * * * *